US008337810B2

(12) United States Patent
Zalutsky et al.

(10) Patent No.: US 8,337,810 B2

(45) Date of Patent: Dec. 25, 2012

(54) STABILIZED COMPOSITIONS AND METHODS FOR RADIOLABELING PHARMACEUTICALS WITH ALPHA-PARTICLE EMITTERS

(75) Inventors: Michael Rod Zalutsky, Chapel Hill, NC (US); Oscar Rodolfo Pozzi, Durham, NC (US)

(73) Assignee: Duke University, Durham, NC (US)

( * ) Notice: Subject to any disclaimer, the term of this patent is extended or adjusted under 35 U.S.C. 154(b) by 1024 days.

(21) Appl. No.: 12/158,186

(22) PCT Filed: Dec. 22, 2006

(86) PCT No.: PCT/US2006/048811

§ 371 (c)(1), (2), (4) Date: Oct. 27, 2008

(87) PCT Pub. No.: WO2007/120251

PCT Pub. Date: Oct. 25, 2007

(65) Prior Publication Data

US 2009/0304585 A1 Dec. 10, 2009

Related U.S. Application Data

(60) Provisional application No. 60/752,370, filed on Dec. 22, 2005.

(51) Int. Cl.
*A61K 51/00* (2006.01)
*A61M 36/14* (2006.01)

(52) U.S. Cl. .................... 424/1.65; 424/1.69; 424/1.85; 424/9.34; 424/1.37

(58) Field of Classification Search .................. 424/1.69
See application file for complete search history.

(56) References Cited

U.S. PATENT DOCUMENTS 4,826,672 A 5/1989 Milius et al.
5,262,175 A * 11/1993 Solanki ...................... 424/1.65

FOREIGN PATENT DOCUMENTS

WO 9200759 A1 1/1992
WO 0204030 A1 1/2002

OTHER PUBLICATIONS

Talanov et al. Nucl. Med. Biol. 2004, 1061-1071.*
Nefedov et al. Russ Chem Rev 1968 37(2) 87-98.*
McDonnell et al. JACS 1954 4651-4658.*
Zalutsky et al. J. Nucl. Med. 2001, 1508-1515.*
Zalutsky, M.R. et al., "Astatination of proteins using an N-succinimidyl tri-n-butylstannyl benzoate intermediate," Applied Radiation and Isotopes, International Journal of Radiation Applications and Instrumentation, Part A., Pergamon Press Ltd., GB, vol. 39, No. 3, Jan. 1988.
Supplementary European Search Report; EP 06 85 0596; The Hague; Sep. 7, 2009, pp. 1-3.
Pozzi et al., Radiopharmaceutical Chemistry of Targeted Radiotherapeutics, Part 2: Radiolytic Effects of 211At-Particles influence N-Succinimidyl 3-211At-Astatobenzoate Synthesis, Journal of Nuclear Medicine Aug. 2005, vol. 46, No. 8, pp. 1393-1400, especially p. 1394, col. 2 and p. 1395, col. 1.
Appelman. The Oxidation States of Astatine in Aqueous Solution, Journal of the American Chemical Society, Feb. 1961, vol. 83, No. 4, pp. 805-807, especially p. 806, col. 2 and abstract.
Akagi et al.; (Jun. 20, 1982) Partial Translation—Oxidizing agent, oxidant—Reducing agent; Source: Pharmaceutical Dictionary, First Edition, p. 223, Publisher: Japan Engineering Technology Federation.
Hadley et al.; (1991) "Astatine-211 Labeling of an Antimelanoma Antibody and Its Fab Fragment Using N-Succinimidyl p-Astatobenzoate: Comparison in Vivo wit the p-[125I]Idobenzoyl Conjugate"; Source: Bioconjugate Chem., vol. 2, pp. 171-179.
Larsen et al.; (1996) "Evaluation of an Internal Cyclotron Target for the Production of 211 At via the 209Bi (α,2n) 211At Reaction"; Source: Appl. Radiat. Isot., vol. 47, No. 2, pp. 135-143.
Pozzi & Zalutsky; (Apr. 2005) "Radiopharmaceutical Chemistry of Targeted radiotherapeutics, Part 1: Effects of Solvent on the Degradation of Radiohalogenation Precursors by 211At α-Particles"; Source: J. Nucl. Med., vol. 46, No. 4, pp. 700-706.
Welch, Michael J.; (Aug. 2005) "Potential and Pitfalls of Therapy with α-Particles"; Source: J. Nucl. Med., vol. 46, No. 8, pp. 1254-1255.

* cited by examiner

*Primary Examiner* — Michael G Hartley
*Assistant Examiner* — Sean R Donohue
(74) *Attorney, Agent, or Firm* — Banner & Witcoff, Ltd.

(57) ABSTRACT

Oxidants (e.g., N-chlorosuccinimide) can be used to stabilize α-particle emitters (e.g., $^{211}$ At) in solution, prior to their subsequent reaction to form α-particle emitter labeled compounds (e.g., a radiolabeled pharmaceutical or a radiolabeled pre-cursor used to prepare it). In particular, the use of an oxidant has been found to maintain the α-particle emitter in a chemical form that facilitates this reaction, which may involve a number of possible mechanisms including electrophilic substitution, nucleophilic substitution, complexation, exchange, or metallic bonding. Compounds labeled with α-particle emitters in this manner have wide-ranging therapeutic applications, particularly in the treatment of cancer.

25 Claims, 14 Drawing Sheets

STABILIZED COMPOSITIONS AND METHODS FOR RADIOLABELING PHARMACEUTICALS WITH ALPHA-PARTICLE EMITTERS

CROSS-REFERENCE TO RELATED APPLICATIONS

This application is a U.S. National Stage application under 35 U.S.C. §371 of International Application No. PCT/US2006/048811 (published as WO 2007/120251 A2), filed Dec. 22, 2006, which claims the benefit of priority of U.S. Provisional Application Ser. No. 60/752,370, filed Dec. 22, 2005, hereby incorporated by reference in its entirety.

This invention was made under contract 2R37-CA42324-17 with an agency (National Institutes of Health) of the United States Government. The United States Government therefore retains certain rights in the invention.

FIELD OF THE INVENTION

The present invention relates to the stabilization of α-particle emitters (e.g., $^{211}$At) used for radiolabeling pharmaceuticals (e.g., monoclonal antibodies) that deliver radiation to targeted areas in the body, such as tumor cells.

BACKGROUND OF THE INVENTION

Alpha particles (i.e., helium nuclei) are significantly more effective in killing tumor cells than either conventional external beam therapy or beta particle emitters such as $^{90}$Y and $^{131}$I, which are employed in the commercially available radioimmunotherapy agents Zevalin® and Bexxar®, respectively. This is due to the high linear energy transfer (~100 keV/μm) and short path length (<100 μm) of α-particles. They can thus focus large amounts of energy over only a few cell diameters. These properties allow for the targeting of specific tumor cells with minimal damage to surrounding healthy tissues.

Of the potential α-particle emitters, $^{211}$At is especially desirable for targeted radiotherapy. $^{211}$At, produced by the cyclotron bombardment of stable $^{209}$Bi with an α-particle beam, has a half-life of 7.2 hours. Theoretically, this is sufficient to allow for the preparation of radiopharmaceuticals and even for their delivery to remote sites with a therapeutically effective level of radioactivity. These considerations have led to the investigation of attaching $^{211}$At to various molecules. Zalutsky, M. et al., Curr Pharm Des. 6:1433-1455 (2000); Wilbur, D., et al., Nucl Med Biol. 20:917-927 (1993); Wilbur, D. et al., Bioconjug Chem. 15:203-223 (2004); and Link, E., Hybridoma 18:77-82 (1999). The toxicity of $^{211}$At-labeled pharmaceuticals to cancer cells has been studied in cell cultures. Larsen, R. et al., Int J Radiat Biol. 72:79-90 (1997); Larsen, R. et al., Radiat Res. 149:155-162 (1998); Walicka, M. et al., Radiat Res. 150:263-268 (1998); and Zalutsky, M. et al., Proc Am Assoc Cancer Res. 43:481 (2002). Treatment of tumors in animal models with these agents has also been performed. Larsen, R. et al., Br J Cancer 77:1115-1122 (1998); Garg, P. et al, Cancer Res. 50:3514-3520 (1990); Andersson, H. et al., Anticancer Res. 21:409-412 (2001). A clinical trial with $^{211}$At-labeled monoclonal antibodies has been undertaken at Duke University Medical Center. Zalutsky, M. et al., Neuro-Oncology 4(suppl):S103 (2002) and Zalutsky, M. Br J Cancer 90:1469-1473 (2004).

As a practical matter, however, the potential benefits of $^{211}$At therapy have not been realized. The alpha radiation that $^{211}$At produces converts astatine into a chemical form that is not easily incorporated into pharmaceuticals or precursor compounds. As a result, the yield of the $^{211}$At-labeled pharmaceutical or $^{211}$At-labeled precursor compound decreases dramatically with increasing radiation dose.

The general importance of radiolytic effects in the preparation of radiolabeled pharmaceuticals has been reported. Bayly, R. et al., J Labelled Compd. 2:1-34 (1966). Also, the stability of positron-emitting radiopharmaceuticals has been studied, including the effects of radical scavengers on stability. Fukumura, T., et al., Appl Radiat Isot. 61:1279-1287 (2004); Bogni, A. et al, J Radioanal Nucl Chem. 256:199-203 (2003); Fukumura, T. et al, Nucl Med Biol. 30:389-395 (2004); and Fukumura, T. et al., Radiochim Acta 92:119-123 (2004). More recently, the effects of solvent type, radiation dose, and other variables on the yield of $^{211}$At-labeled precursor compounds of significant interest for cancer therapy have been evaluated. Pozzi, O. et al., J Nucl Med. 46:1393-1400 (2005) and Pozzi, O. et al., J Nucl Med. 46:700-706 (2005).

Substantial difficulties remain in the production of pharmaceuticals labeled with $^{211}$At or other α-particle emitters at radioactivity levels sufficient for therapeutic applications. These high radioactivity levels, over the course of reagent solution preparation, storage, and use in preparing radiolabeled pharmaceuticals, invariably result in a cumulative radiation dose from α-particles that is detrimental to the labeling chemistry. Undesired radiolytic effects include loss of precursor (e.g., organic tin compounds) and reactive $^{211}$At through their interaction with free radicals, generated by the radiolysis of the reaction solution. For example, in the case of alpha radiation absorbed by methanol, especially under acidic conditions, the formation of reducing species (e.g., hydrogen and formaldehyde) is believed to contribute to the losses in the yield of $^{211}$At-labeled compounds.

The detrimental radiolytic effects described above have greatly complicated the synthesis of α-particle emitter labeled pharmaceuticals having therapeutically effective levels of radioactivity. This is especially true in cases where it is desired to prepare these pharmaceuticals in a location that is remote from the site of production of the α-particle emitter. The time required for shipping necessarily increases the radiation dose received by the α-particle emitter-containing reagent solution, thereby promoting the radiolytic effects that have shown to decrease yields of the α-particle emitter labeled pharmaceutical end product.

BRIEF SUMMARY OF THE INVENTION

Despite previous unsuccessful attempts to realize the fill potential of α-particle emitter labeled pharmaceuticals in therapy, it is now recognized that $^{211}$At and other α-particle emitters can be stabilized in a manner that allows the preparation of such pharmaceuticals in high yields and at high levels of radioactivity. The detrimental effects of radiolysis on the labeling chemistry are overcome, even at α-particle radiation doses previously considered prohibitive. As a result of stabilization according to the present invention, a substantially increased amount of α-particle emitter radioactivity can be incorporated into the desired α-particle emitter labeled compounds, such as those formed by the reaction of the α-particle emitter with an organometallic precursor. The correspondingly high levels of radioactivity of the α-particle emitter labeled pharmaceuticals made from these precursors are suitable for practical therapeutic applications. Because of the stabilizing effects according to the present invention, α-particle emitter labeled pharmaceuticals can be prepared well after the time (or far away from the site) of production of the α-particle emitter.

In particular, the invention is based on the discovery that α-particle emitters can be stabilized in solutions containing an oxidant, prior to subsequent reactions to form α-particle emitter labeled compounds (i.e., a radiolabeled pharmaceutical or a radiolabeled precursor used to prepare it). The use of an oxidant has been found to maintain the α-particle emitter in a chemical form that facilitates these reactions, which may, for example, involve electrophilic substitution. This chemical form may have a higher oxidation state, relative to the significantly less reactive (or completely unreactive) α-particle emitter species that are otherwise generated over time from the effects of radiolysis. The production of one or more of these less reactive or unreactive species of the α-particle emitter can be minimized by stabilizing the α-particle emitter soon after it is made.

In one embodiment, therefore, the present invention is a method for preparing an α-particle emitter labeled compound. The method comprises stabilizing an α-particle emitter in a solution containing an oxidant and thereafter reacting the α-particle emitter with a compound that is reactive with the α-particle emitter to provide the α-particle emitter labeled compound. In another embodiment, the solution comprises an alcohol (e.g., methanol). In another embodiment, the oxidant is a halogenated organic compound (e.g., N-chlorosuccinimide). In another embodiment, the compound that is reactive with the α-particle emitter has an electrophilic substitution site. In another embodiment, the compound having an electrophilic substitution site is a pharmaceutical (e.g., an antibody or a peptide) that is modified to have the electrophilic substitution site. In another embodiment, the compound having the electrophilic substitution site is an organometallic precursor (e.g., an organic tin compound such as N-succinimidyl 3-(tri-methylstannyl)benzoate or N-succinimidyl 3-(tri-n-butylstannyl)benzoate). In another embodiment, the α-particle emitter is $^{211}$At. In another embodiment, the compound that is reactive with $^{211}$At has a reactive astatination site. In another embodiment, the reactive astatination site is selected from the group consisting of an electrophilic astatine substitution site, a nucleophilic astatine substitution site, an astatine complexation site, an astatine exchange site, and an astatine-metal bonding site.

In another embodiment, the present invention is method for preparing a pharmaceutical that is radiolabeled with an α-particle emitter. The method comprises stabilizing the α-particle emitter in a solution containing an oxidant, thereafter reacting the α-particle emitter with an organometallic precursor to yield an intermediate (e.g., an α-particle emitter labeled precursor), and coupling the pharmaceutical with the intermediate (e.g., the α-particle emitter labeled precursor) to provide the pharmaceutical that is radiolabeled with the α-particle emitter. In another embodiment, the method further comprises, after the reacting step, evaporating the solution from the intermediate (e.g., the α-particle emitter labeled precursor). In another embodiment, the pharmaceutical is an antibody (e.g., a monoclonal antibody) or a peptide. In another embodiment, the pharmaceutical that is radiolabeled has an initial radioactivity level of at least 5 mCi (185 MBq). In another embodiment, at least 30% of the α-particle emitter in the solution is used to radiolabel the pharmaceutical.

In another embodiment, the present invention is a method for stabilizing $^{211}$At prior to using it for an astatination reaction. The method comprises combining $^{211}$At with a solution containing an oxidant and storing the solution containing the oxidant for a period of time sufficient to receive a radiation dose of at least about 2,000 Gy.

In another embodiment, the present invention is a method for providing an α-particle emitter for the synthesis of an α-particle emitter labeled compound. The method comprises combining, at a first location, the α-particle emitter with a solution containing an oxidant to yield a stabilized composition, and transporting the stabilized composition to a second location.

In another embodiment, the present invention is a stabilized composition comprising $^{211}$At and a solution containing an oxidant. The composition is essentially free of a compound having a reactive astatination site.

In another embodiment, the present invention is a stabilized composition consisting essentially of an α-particle emitter, an alcohol, and an oxidant.

In another embodiment, the present invention is a kit for preparing a labeling compound for labeling a pharmaceutical. The kit comprises a first composition comprising an α-particle emitter, an alcohol, and an oxidant and a second composition comprising a compound that is reactive with the α-particle emitter. The first composition and the second composition are packaged in the kit in separate containers. In another embodiment, the α-particle emitter is $^{211}$At and the compound that is reactive with the α-particle emitter has a reactive astatination site.

In another embodiment, the present invention is a method of isolating an α-particle emitter in a stabilized form. The method comprises preparing the α-particle emitter by irradiation of a cyclotron or other particle accelerator target (e.g., an element), purifying the α-particle emitter, and eluting the α-particle emitter in a solution containing an oxidant. In another embodiment, the purifying step comprises distillation.

These and other embodiments are apparent from the following Detailed Description.

BRIEF DESCRIPTION OF THE DRAWINGS

FIG. 6 shows the relationship between the radiation dose received by the methanol, in which $^{211}$At was stored, and the yield of SAB obtained from electrophilic astatination of BuSTB with $^{211}$At.

Figure 9:
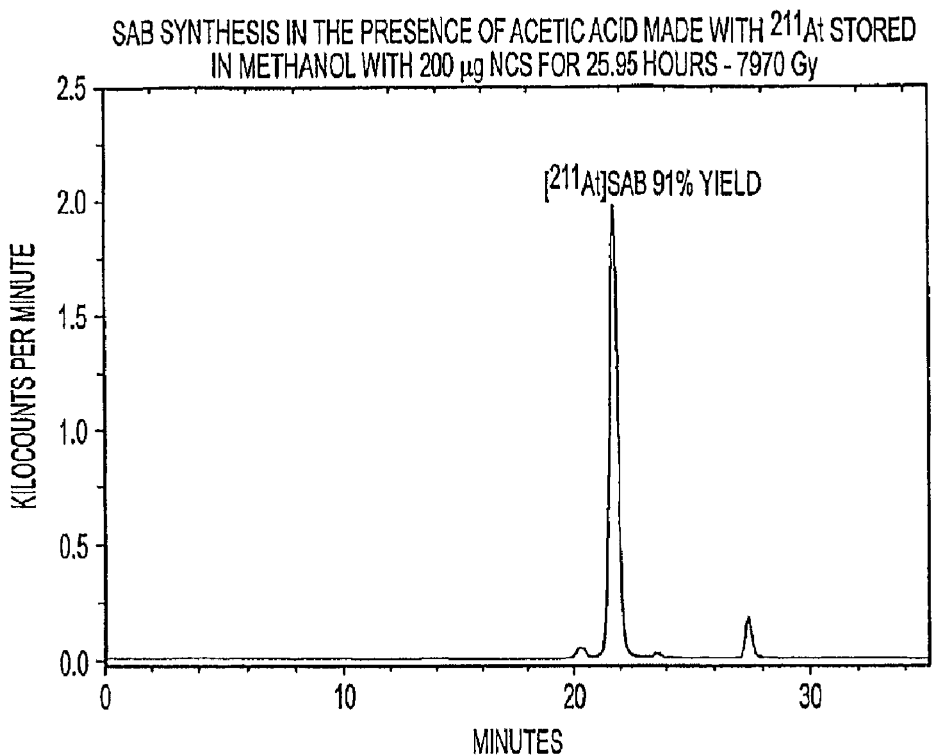
Figure 9:
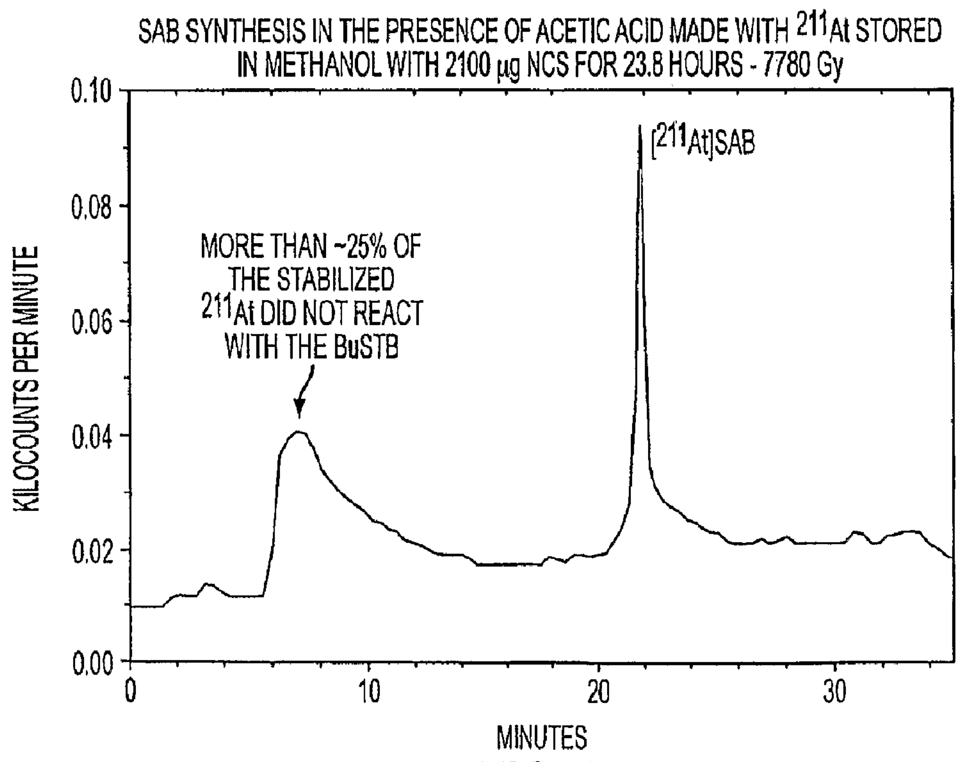

FIG. 9 shows HPLC chromatograms of the electrophilic astatination reaction products using $^{211}$At in methanol that was stabilized with 2,100 μg and 200 μg NCS, stored for 23.8 hours and 25.95 hours respectively, and reacted with BuSTB to form SAB. The calculated radiation doses received by the NCS-containing methanol, in which $^{211}$At was stabilized, were 7,780 and 7,970 Gy, respectively, during storage and reaction.

Figure 10:
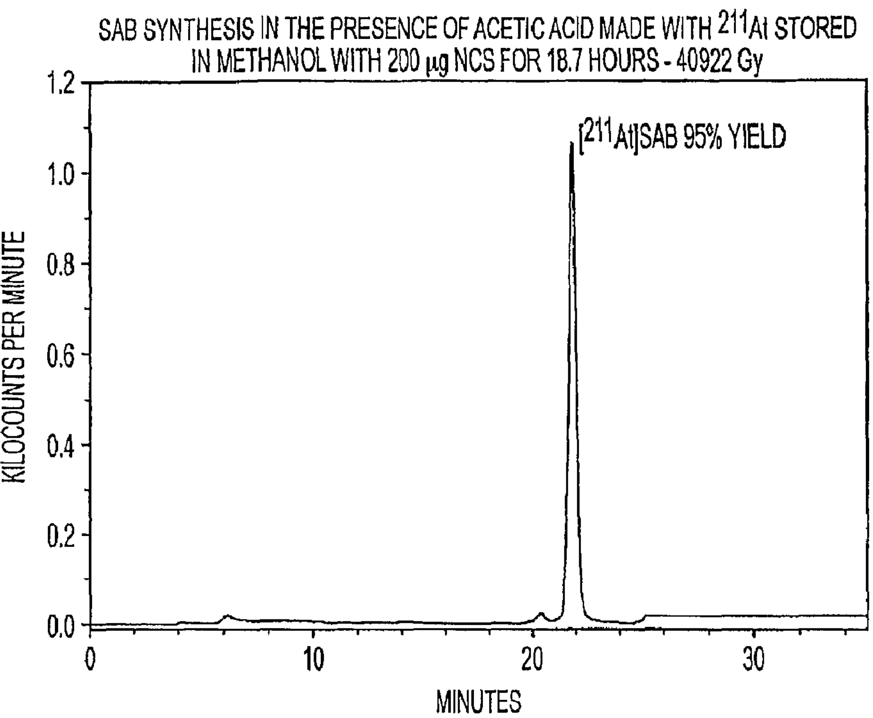
Figure 10A:
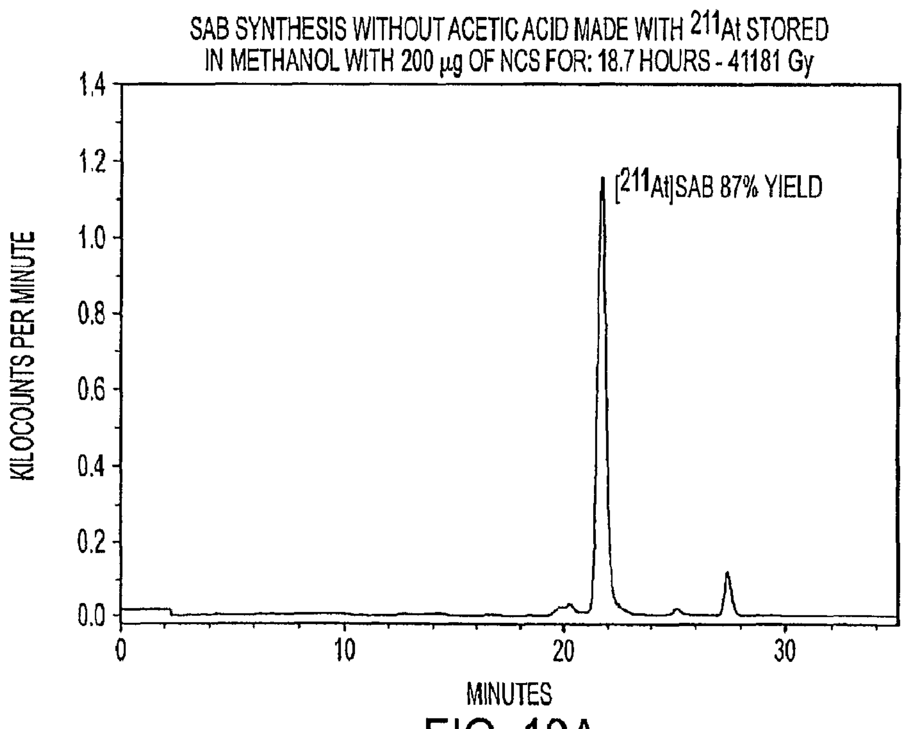
Figure 10B:
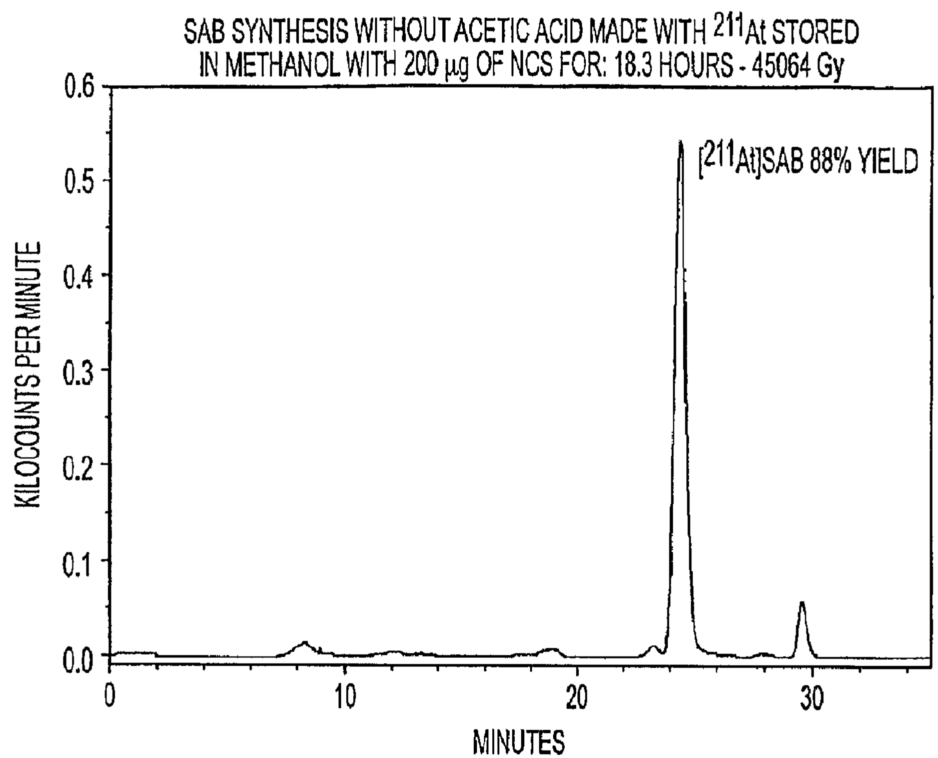

FIG. 10 shows HPLC chromatograms of the electrophilic astatination reaction products, under both acidic (one reaction) and neutral (two reactions) conditions, using $^{211}$At in methanol that was stabilized with 200 μg NCS, stored for 18.7 hours (in the case of the one reaction under acidic conditions and one of the two reactions under neutral conditions) and 18.3 hours (in the case of the other of the two reactions under neutral conditions), and reacted with BuSTB to form SAB. The calculated radiation doses received by the NCS-containing methanol, in which the $^{211}$At was stabilized, were 40,922 Gy, 41,181 Gy and 45,064 Gy respectively, during storage and reaction.

Figure 11:
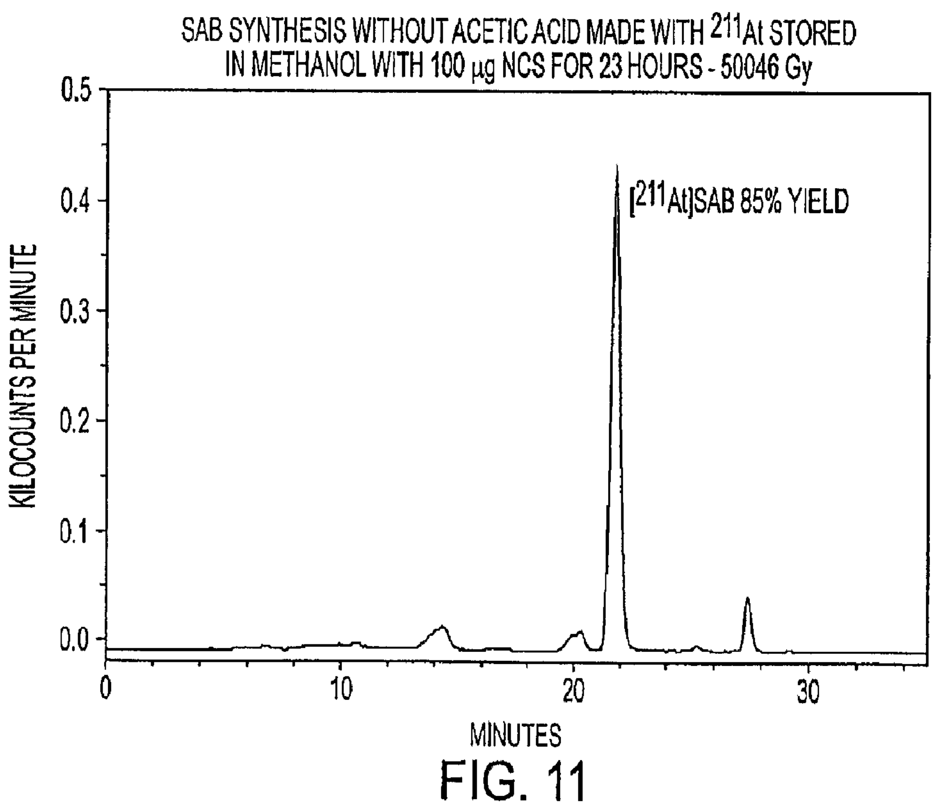

FIG. 11 shows the HPLC chromatogram of the electrophilic astatination reaction product using $^{211}$At in methanol that was stabilized with 100 μg NCS, stored for 23 hours, and reacted with BuSTB to form SAB. The calculated radiation dose received by the NCS-containing methanol, in which the $^{211}$At was stabilized, was 50,046 Gy during storage and reaction.

Figure 12:
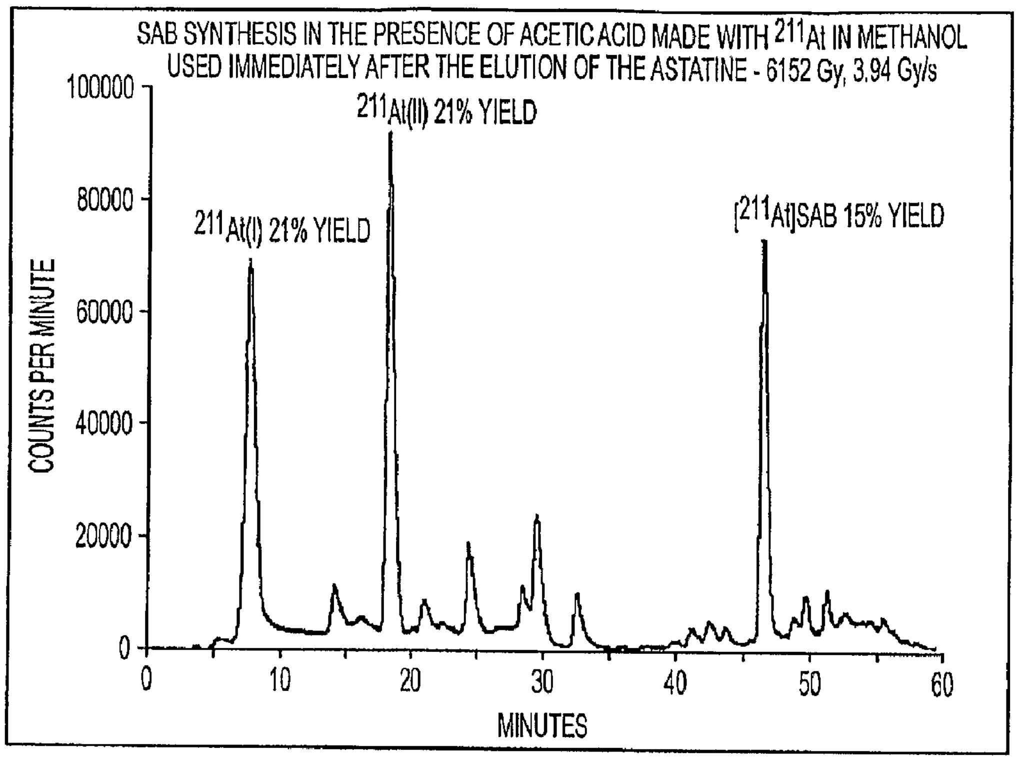

FIG. 12 shows the HPLC chromatogram of the electrophilic astatination reaction product, obtained using $^{211}$At in methanol without an oxidant, where the radiolabeling reaction was performed almost immediately after elution of the freshly prepared $^{211}$At. The calculated radiation dose rate and total dose, received by the methanol, were 6152 Gy and 3.94 Gy/s, respectively.

Figure 13:
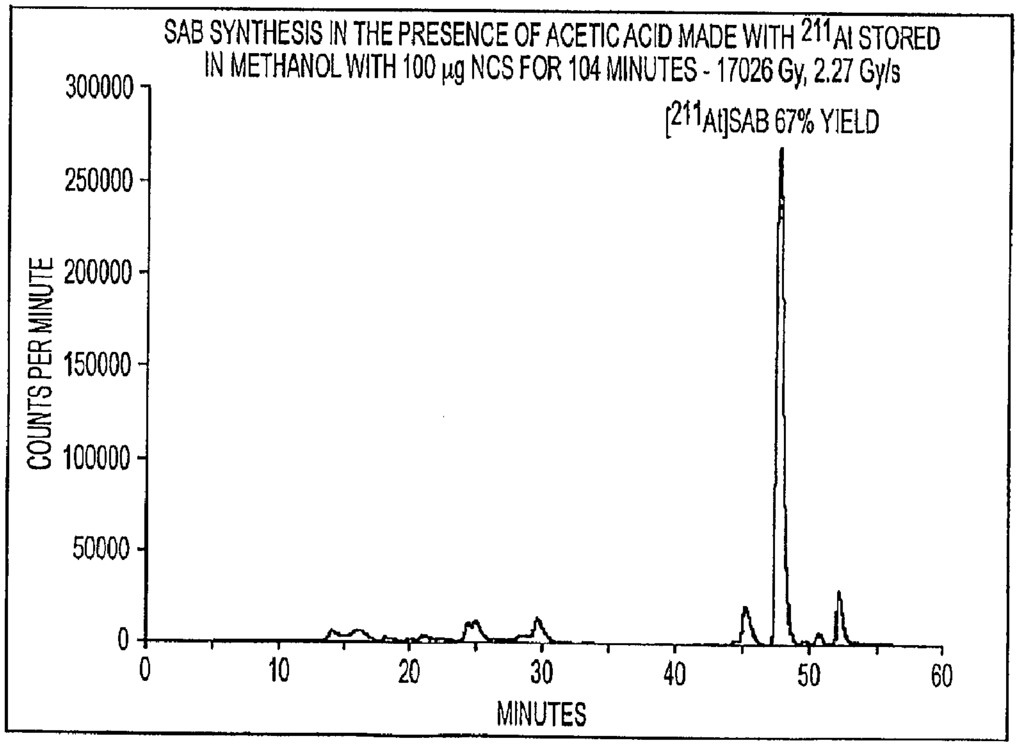

FIG. 13 shows the HPLC chromatogram of the electrophilic astatination reaction product, obtained using $^{211}$At in methanol with the oxidant NCS added 21 minutes after elution of the freshly prepared $^{211}$At (during which time the methanol had received a calculated dose rate and radiation dose of 366 Gy/s and 4613 Gy, respectively), where the radiolabeling reaction was performed after a 104 minute storage period following NCS addition. The calculated radiation dose rate and total dose, received by the methanol, were 2.27 Gy/s and 17026 Gy, respectively.

Figure 14:
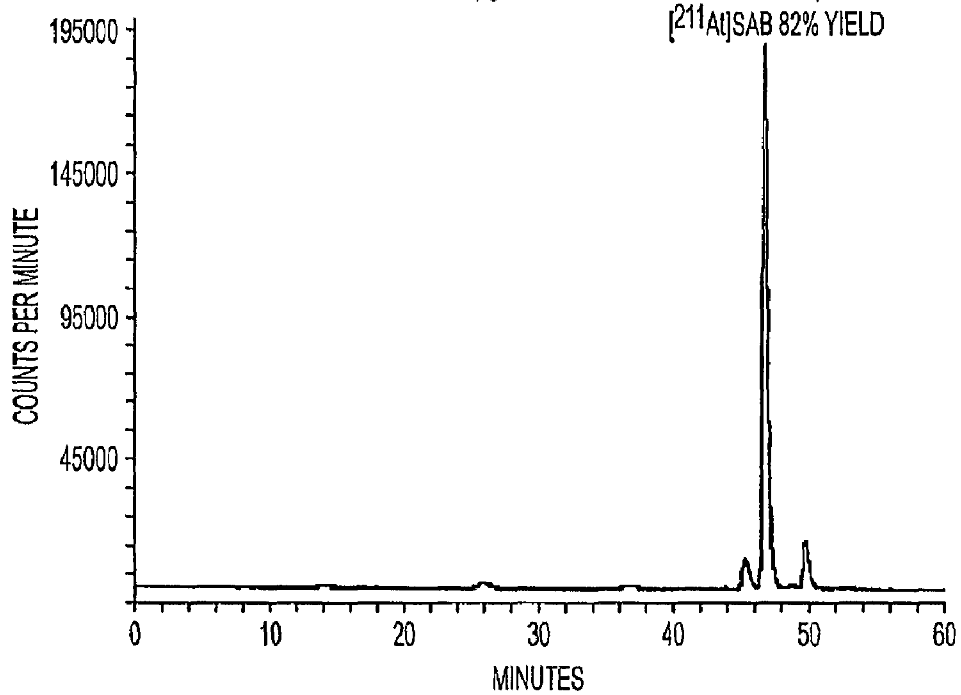

FIG. 14 shows the HPLC chromatogram of the electrophilic astatination reaction product using $^{211}$At in methanol that was stabilized with 100 μg NCS, stored for 18 hours, and reacted with BuSTB to form SAB. The calculated radiation dose received by the NCS-containing methanol, in which the $^{211}$At was stabilized, was 125,086 Gy during storage and reaction.

Figure 15:
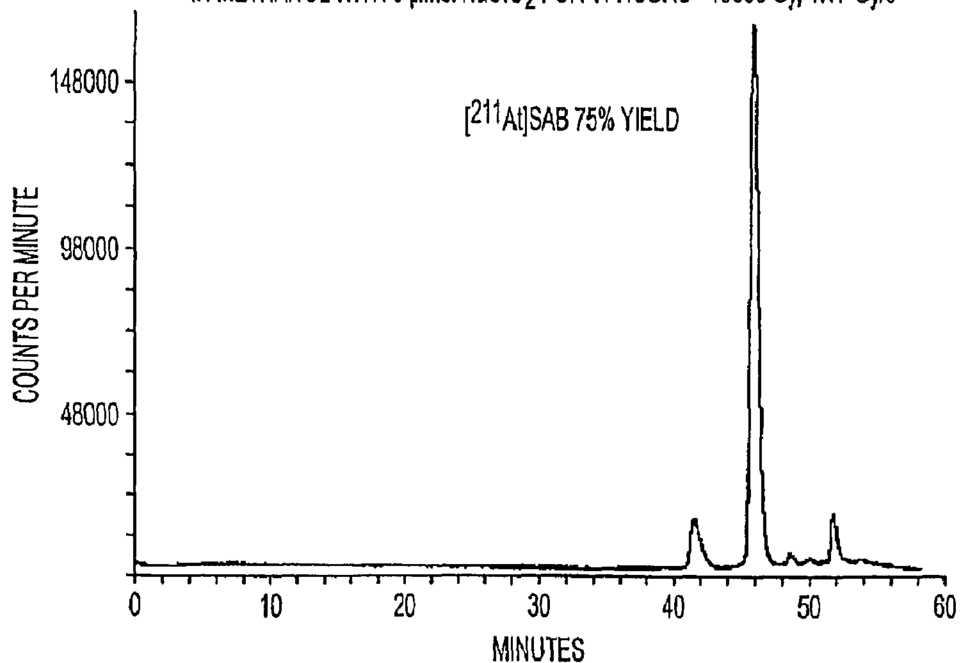

FIG. 15 shows the HPLC chromatogram of the electrophilic astatination reaction product using $^{211}$At in methanol that was stabilized with 5 μmol sodium chlorite, stored for 11 hours, and reacted with BuSTB to form SAB. The calculated radiation dose rate and total dose, received by the $NaClO_2$-containing methanol, in which the $^{21}$At was stabilized, were 1.17 Gy/s and 48,553 Gy, respectively, during storage and reaction.

Figure 16:
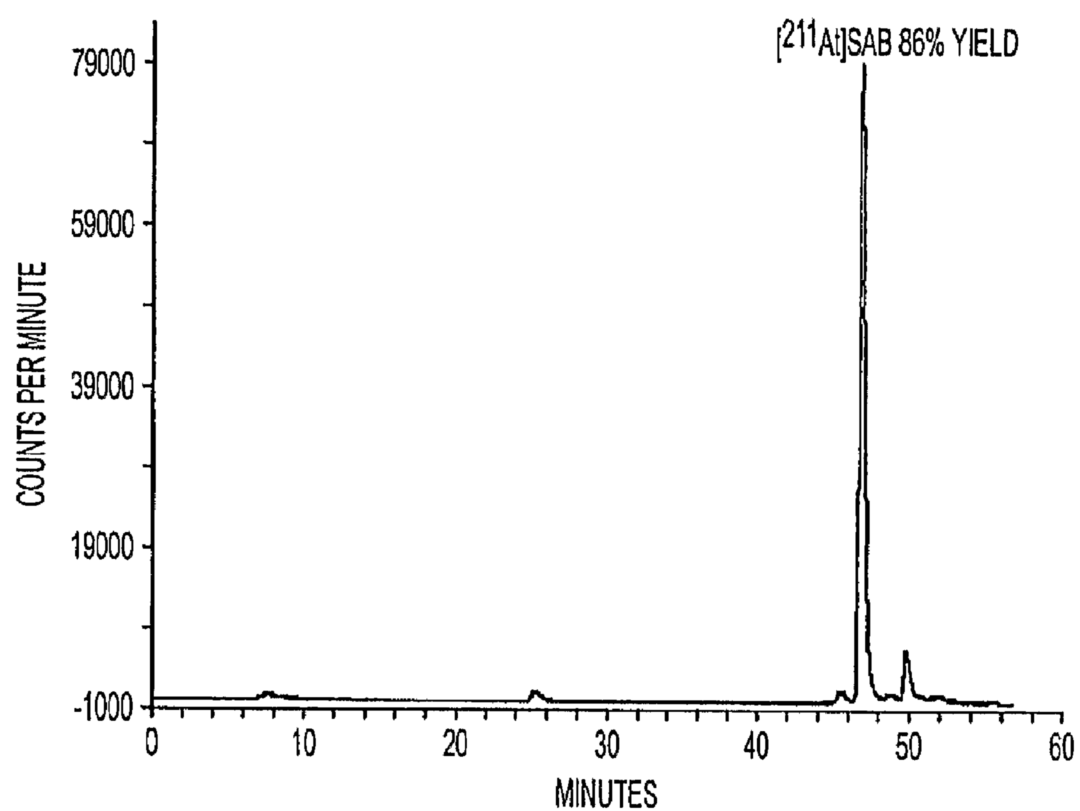

FIG. 16 shows the HPLC chromatogram of the electrophilic astatination reaction product using $^{211}$At in methanol that was stabilized with 5 μmol ammonium cerium (IV) nitrate, stored for 7.52 hours, and reacted with BuSTB to form SAB. The calculated radiation dose rate and total dose, received by the $(NH_4)_2Ce(NO_3)_6$-containing methanol, in which the $^{211}$At was stabilized were 2.6 Gy/s and 71,997 Gy, respectively, during storage and reaction.

DETAILED DESCRIPTION OF THE INVENTION

The present invention is based on the finding that α-particle emitters can be effectively stabilized against, or protected from, detrimental effects associated with their own radiation. In particular, these effects are believed to include the reduction of the α-particle emitters to oxidation states that do not readily undergo key reactions necessary for the synthesis of radiolabeled pharmaceuticals. Such reactions may involve direct synthesis via coupling of the α-particle emitter with a pharmaceutical (or a derivative that is better suited to couple with the α-particle emitter). Otherwise, indirect synthesis routes involve the preparation of an intermediate or α-particle emitter labeled precursor that can be coupled to another molecule (e.g., a pharmaceutical such as protein or peptide) to form a radiolabeled pharmaceutical.

It is believed that solutions used to store α-particle emitters increase their reducing potential as they undergo alpha irradiation. This is thought to contribute to the formation of relatively less reactive α-particle emitter species, which increases with increasing radiation dose. The generation of free radicals in methanol, for example, can lead to the production of hydrogen and formaldehyde, both of which potentially reduce $^{211}$At. As radiolytic byproducts and consequently the solution reducing potential increase over time, $At^+$ which is reactive with pharmaceuticals and/or precursor molecules (e.g., by electrophilic astatination), is converted to one or more less reactive (and more stable) form(s), thought to include complexes formed between solvent and/or impurities and the astatine species generated by radiolysis.

As a result of radiolytic effects, therefore, the amount of the initially formed α-particle emitter which can be incorporated into a given radiolabeled pharmaceutical decreases over time. Moreover, the rate of conversion of the α-particle emitter into less reactive form(s) increases at higher radioactivity levels, such as those required to prepare radiolabeled pharmaceuticals for therapeutic applications (e.g., cancer treatment). In addition to radioactivity level, the α-particle emitter storage or shipping time (i.e., the time prior to reaction) also determines the solution radiation dose received and consequently the extent to which the α-particle emitter is converted to less reactive form(s). For these reasons, the art has not satisfactorily addressed the preparation of α-particle emitter labeled pharmaceuticals having therapeutically effective radioactivity levels, from reagent solutions stored for extended periods (e.g., to allow shipping).

The present invention overcomes these difficulties by stabilizing the α-particle emitter in solution with an oxidant. The stabilization may occur immediately upon, or soon after, preparing a solution of the α-particle emitter. Through stabilization, the conversion of the α-particle emitter to less reactive form(s) is suspended, if not prevented from the outset. As a result, stabilized α-particle emitters can be used in preparing radiolabeled pharmaceuticals (or radiolabeled precursors) in high yields.

The yield improvement resulting from stabilization of the α-particle emitter allows for the synthesis of α-particle emitter labeled pharmaceuticals having radioactivity levels suitable for therapeutic applications. Radioactivity levels sufficient even for multiple patient doses, from a single vial, are possible. Moreover, stabilized α-particle emitter solutions can be shipped to remote locations with little or no loss of reactivity for their later use in preparing α-particle emitter labeled pharmaceuticals. Finally, stabilized solutions of α-particle emitters can be used in simple kits whereby packaged reagents (e.g. separate compositions comprising (1) the stabilized α-particle emitter solution and (2) a pharmaceutical or modified pharmaceutical) are transported and combined at the site of use to provide the α-particle emitter labeled pharmaceutical (or an α-particle emitter labeled precursor used to prepare it) with therapeutic levels of radioactivity. The above findings are based on experimental observations at high radioactivity levels and/or over long storage times, where the solution containing the α-particle emitter receives a radiation dose corresponding to 2-50 times, and more typically 5-25 times, the level at which previous approaches failed.

As stated above, α-particle emitters provide potent sources of lethal irradiation against tumor cells and micrometastases because of their short range and densely ionizing radiation. The present invention is applicable to any of the approximately 100 natural and manmade radionuclides (predominantly elements with atomic weights above 82) that decay via α-particle emission. As a class, metallic α-particle emitters are representative of elements that may be stabilized according to the present invention. Selection criteria for specific α-particle emitters for a given application are known to those of skill in the art and include the half-life (i.e., the time required for a radioactive isotope to decay to 50% of its initial quantity), as well as the properties of the resulting "daughter" isotopes. Suitable α-particle emitters include $^{211}$At (half-life of 7.2 hours), $^{213}$Bi (half-life of 46 minutes), $^{212}$Bi (half-life of 60 minutes), $^{223}$Ra (half-life of 11.4 days), $^{225}$Ac (half-life of 10.0 days), and $^{212}$Pb (half-life of 61 minutes). While $^{212}$Pb actually decays by first emitting a beta particle, the resulting isotope, namely $^{212}$Bi, is an α-particle emitter. The halogen $^{211}$At has provided significant promise in the area of targeted radiotherapy.

According to the present invention, stabilization of the α-particle emitter occurs prior to its use in forming a radiolabeled pharmaceutical or radiolabeled precursor of the pharmaceutical. Advantageously, the α-particle emitter may be stabilized with oxidant as soon as a reagent solution (e.g., a methanol solution) of the α-particle emitter is prepared or shortly thereafter. Thus, the stabilization may involve preparing a reagent solution of the α-particle emitter, wherein the solution already contains the oxidant. Otherwise, the oxidant may be added separately to the solution containing the α-particle emitter. Regardless of the order in which the components of the α-particle emitter reagent solution are added, the important consideration is to avoid prolonged or otherwise excessive exposure of the α-particle emitter-containing solution to alpha irradiation in the absence of an oxidant.

When the α-particle emitter is prepared by bombardment (i.e., irradiation) of a target material (e.g., an element such as $^{209}$Bi) and purification (e.g., separation of the desired radionuclide from the target by distillation), stabilization according to the present invention may comprise direct elution of the prepared and purified α-particle emitter into an oxidant-containing solution. In this case, the α-particle emitter can be isolated in a stabilized form, whereby all solution irradiation occurs in the presence of an oxidant. This protects the solution and consequently the α-particle emitter from detrimental radiolytic effects from the outset. For example, $^{211}$ At may be stabilized by eluting this isotope directly into an oxidant-containing solution, following its synthesis by cyclotron bombardment of a $^{209}$Bi target and recovery by volatilization and cooling. The use of an oxidant-containing alcohol solution to elute (or wash out) $^{211}$At from a cryogenically cooled distillation reservoir (i.e., a cryotrap) provides a convenient method for stabilizing this α-particle emitter.

The balance of the solution (i.e., aside from the oxidant) in which the α-particle emitter is stabilized is not critical. Preferably, the desired radiolabeled compounds that are produced from reaction of the α-particle emitter are partially, if not completely, soluble in the reaction medium. This consideration, as well as others relating to adapting the solution to a particular radiolabeling application are known to those of skill in the art. Suitable solutions comprise alcohols and especially the lower aliphatic alcohols such as methanol, ethanol, 1-propanol, 2-propanol, n-butanol, and i-butanol. Secondary and tertiary alcohols may also be used, as well as polymeric alcohols (e.g., polyvinyl alcohol) of varying degrees of polymerization. Methanol has the ability to dissolve compounds over a wide range of hydrophilicity/hydrophobicity and is therefore particularly useful, in combination with an oxidant, for stabilizing α-particle emitters. The pH of the solution is also not critical, as the α-particle emitter can be stored and later reacted over a wide pH range. In general, somewhat acidified solutions, for example those having a pH from about 4 to about 7, and typically from about 5 to about 6.5, are suitable for storage and subsequent reaction. Highly acidic conditions during storage may accelerate the conversion of the α-particle emitter to relatively less reactive form(s).

It has been determined that even a small amount of oxidant in solution is effective for overcoming adverse radiolytic effects, as described above, on α-particle emitter reactivity. The oxidant may be present in an amount of at least 0.001% by weight of the oxidant-containing solution. Generally, the amount can range from about 0.0001% to about 50% by weight, typically from about 0.005% to about 10% by weight, and often ranges from about 0.01% to about 1% by weight. For example, the use of about 0.02% by weight of oxidant to stabilize $^{211}$At, within about 10 minutes of its elution in methanol following cyclotron synthesis, effectively preserves the electrophilic astatination reactivity of this α-particle emitter, for the preparation of key $^{211}$At labeled precursors. Stabilization is achieved at α-particle radiation doses to the oxidant-containing methanol solution exceeding 40,000 Gy, and even 45,000 Gy. In the absence of an oxidant, this dose level would convert a large portion of the $^{211}$At into forms that do not readily undergo subsequent radiolabeling reactions such as those involving electrophilic astatination, thereby significantly lowering the potential yield of $^{211}$At-labeled pharmaceuticals. Depending on the particular oxidant chosen, one of ordinary skill, in view of the present disclosure, could readily determine an effective range for the amount of oxidant to be added, for stabilization of the α-particle emitter against loss of reactivity.

Amounts of oxidant in the ranges given above preserve the chemical reactivity of the α-particle emitter from the time of its stabilization in an oxidant-containing solution until its use in subsequent radiolabeling reactions. During this period, the oxidant-containing solution nominally receives an α-particle radiation dose of at least about 2,000 Gy, and if the time required for these reactions is considered, the dose will be somewhat higher. Radiolabeling reactions, including the types discussed in more detail below, will normally require reaction times in the range from about 1 minute to about 3 hours, and often from about 5 minutes to about 1 hour. Many such reactions, for example, are completed in a time from about 5 minutes to about 30 minutes. More typically, because of the high initial radioactivity levels required for medical treatment (e.g., cancer treatment) applications as well as the time required to ship α-particle emitter reagent solutions to the destination where they are used to prepare radiolabeled pharmaceuticals, the oxidant-containing solution receives a dose from about 3,000 Gy to about 150,000 Gy, usually from about 3,000 Gy to about 50,000 Gy, and often from about 10,000 Gy to about 50,000 Gy. Radiation dose rates to the oxidant-containing solution will normally exceed about 1 Gray per second (Gy/s). Depending on the solution volume (which is governed at least partly by the particular radiolabeling reaction and choice of oxidant), radiation dose rates may be up to about 10 Gy/s, for example in the representative ranges of from about 2 to about 8 Gy/s and from about 4 to about 6 Gy/s. These doses and dose rates, in the absence of an oxidant in the solution, result in a significantly decreased chemical reactivity of the α-particle emitter, rendering it partially or completely unusable for subsequent chemical reactions needed to prepare radiolabeled pharmaceuticals.

The radiation dose (D) to the solution over a time period (t) may be calculated from knowledge of the radioactivity at the beginning of the period ($A_i$), the first-order decay constant for the α-particle emitter (λ), the mass of solution (m), and the mean energy emitted per nuclear transition ($\Delta_i$), according to the equation $$D = A_i(1 - e^{-\lambda t})\frac{1}{\lambda}\frac{1}{m}\Delta_i,$$

where the units for D, $A_i$, λ, t, and m, may be expressed in gray (Gy), megabecquerel (MBq), seconds$^{-1}$ ($s^{-1}$), seconds (s), and grams (g), respectively. For example, for the α-particle emitter $^{211}$At, a value of $1.09\times10^{-3}$ Gy·g/MBq·s for $\Delta_i$ is used, based on dose contributions from α-particles and α-recoil nuclei. See Weber et al., SOC NUCL MED.: 406-415 (1989). The first-order decay constant (λ) and the half-life ($t_{1/2}$) for a given radionuclide are related by the equation $\lambda=0.693/t_{1/2}$.

The use of an oxidant in solutions for storing α-particle emitters is therefore beneficial for preserving the chemical reactivity of these radionuclides. It is believed that the loss of this chemical reactivity due to radiolysis is not easily recovered and may in fact be irreversible. Therefore, the ability to prevent the generation of relatively less reactive chemical forms of the α-particle emitter affords important commercial advantages in the production of α-particle labeled pharmaceuticals. The fact that an oxidant can provide this important storage stability of α-particle emitters in solution is surprising, since stabilizers and/or preservatives normally function by preventing, rather than promoting, oxidation. Antioxidants are widely employed, for example in the pharmaceutical industry, to scavenge free radicals or metal cations that catalyze oxidation reactions in solution. Likewise, it was previously thought that α-particle emitters gradually lose chemical reactivity due to oxidation. Thus, storage of an α-particle emitter in an oxidant-containing solution would actually have been counterintuitive. In fact, reducing agents, rather than oxidizing agents, are conventionally used in the preparation of therapeutic levels of radioactive drugs. See McDevitt et al, J NUCL MED. 40:1722-1727 (1999).

Oxidants of the present invention possess the requisite oxidizing strength to prevent the generation of certain α-particle emitter forms, shown to have low reactivity for the synthesis of radiolabeled pharmaceuticals. Suitable oxidizing agents therefore include those having a standard reduction potential in aqueous solution of at least about +0.5 volts, more typically from about +0.7 volts to about +3 volts, and usually from about +0.75 volts to about +2 volts. Examples of oxidants that may be used to stabilize the α-particle emitter in solution according to the present invention include halogenated organic compounds (e.g., halosuccinimides) and peroxides such as hydrogen peroxide, alkali and alkaline earth metal peroxides (e.g., sodium peroxide and magnesium peroxide), organic peroxides such as alkyl peroxides (e.g., butyl hydroperoxide) and urea peroxide (carbamide). Acids such as formic, acetic, peracetic, nitric, nitrous, perchloric, periodic, sulfuric, hypochlorous acid, hypobromous acid, and their salts may also be used, as well as acids and salts, such as the ammonium, alkali metal, and alkaline earth metal salts (e.g., the sodium, potassium, calcium, and barium salts), which generate permanganate, chromate, dichromate, perborate, perphosphate, persulfate, perchlorate, chlorate, chlorite, hypochlorite, perbromate, bromate, bromite, hypobromite, periodate, iodate, iodite, hypoiodite, and bismuthate, ions. Other oxidants include molecular oxygen, ozone, chlorine, bromine, and iodine. Gaseous oxidants such as molecular oxygen may advantageously be incorporated into the carrier gas used in the recovery of $^{211}$At via distillation, as described above.

Further examples of oxidants include halo-substituted amines; sulfonyl and sulfinyl halides of the formulas R—($SO_2$)—X and R—(SO)—X, respectively, where X is a halide and R is an organic moiety such as an alkyl radical (e.g., methyl, ethyl, propyl, isopropyl, etc.), an aryl radical (e.g., phenyl), or other organic or substituted organic radical; phosphorous-containing halide compounds of the formula R—P—X, where X and R are as defined above; haloformate compounds of the formula X—$CO_2$—R, where X and R are as defined above. Other chemical reagents known to promote oxidation, such as compounds that generate metal ions (e.g., $Fe^{+2}$, $Fe^{+3}$, $Ce^{+4}$, $T^{+3}$, $Cu^{+}$, $Cr^{+6}$, $Mn^{+3}$, $Mn^{+4}$, $Ru^{+3}$, $Ru^{+4}$ and $V^{+5}$) in the reaction solution, and particularly metal oxides exhibiting these metallic oxidation states (e.g., $MnO_2$, and $V_2O_5$) are also suitable. Various other oxidizing agents include iodosylbenzene, iodoxybenzoic acid, methylmorpholine oxide, chloroperbenzoic acid, oxalyl chloride, dimethyl sulfoxide, pivaldehyde, potassium peroxomonosulfate, tetrabutylammonium peroxydisulfate, tetramethylpiperidinyloxy, triacetoxyperiodinane, trifluoroacetic peracid, and trimethylacetaldehyde. Combinations of the above oxidants may also be used. Halogenated organic compounds such as halosuccinimides are particularly suitable oxidants. These include N-chlorosuccinimide (NCS), N-bromosuccinimide (NBS), and derivatives of these oxidants, such as their alkyl-substituted derivatives (e.g., 2,3-dimethyl N-chlorosuccinimide). Where an acid is used as an oxidant, very low pH values (e.g., less than 2.5) should generally be avoided, unless the acid is combined with another, non-acid oxidant (e.g., NCS).

The term "oxidant" for purposes of this disclosure is also meant to embrace agents that, when added to the solution used for the radiolabeling reaction, will generate oxidizing species in situ. For example, hydroxide compounds such as sodium hydroxide or potassium hydroxide, are considered oxidants, because hydroxide ion, when subjected to radiation from the α-particle emitter in the reaction solution, can lead to the formation of peroxide radicals and hydrogen peroxide, which are strongly oxidizing species. In view of the present disclosure, including the detailed experimental procedures and results discussed below with respect to various oxidants tested, one could routinely tailor the radiolabeling reaction system to a particular oxidant chosen. For example, appropriate pH ranges and solvent types for the reaction system could be established for a given oxidant, in order to address issues such as pH control and oxidant solubility.

As described above, the use of an oxidant in solution can prevent the unwanted conversion over time of the α-particle emitter into chemically less reactive or even unreactive forms. Without the oxidant, the extent of this conversion depends highly on the total radiation dose received by the solution containing the α-particle emitter, such that the rate of conversion is strongly a function of the radioactivity level of the α-particle emitter. At initial α-particle emitter solution radioactivity levels from about 15 mCi (560 MBq) to about 270 mCi (10 GBq) needed to prepare radiolabeled pharmaceuticals for practical applications (e.g., radiolabeled monoclonal antibodies for the treatment of tumor cells), a substantial portion of the α-particle emitter may be converted, in the absence of an oxidant, into a relatively less reactive form over a few hours.

The use of an oxidant, however, effectively prevents the conversion of the α-particle emitter to these relatively less reactive form(s) in solutions having the above levels of initial radioactivity (i.e., as measured immediately after preparation of the solution containing the α-particle emitter). Solutions of α-particle emitters having higher initial radioactivity levels (e.g., from about 270 mCi (10 GBq) to about 2700 mCi (100 GBq)) may also be stabilized, for example, in cases where sufficient radioactivity for multiple patient doses or extended storage times are desired. More typically, however, initial solution radioactivity levels range from about 20 mCi (750 MBq) to about 270 mCi (10 GBq), and usually from about 40 mCi (1.5 GBq) to about 200 mCi (7.5 GBq). Often, initial radioactivity levels in the range of about 20 mCi (750 MBq) to about 25 mCi (950 MBq) will be sufficient for the preparation of therapeutically effective radiolabeled pharmaceuticals or radiolabeled precursors.

A significant practical advantage of the present invention therefore resides in the ability to store the α-particle emitter in solution at high radioactivity levels and/or for extended periods, without suffering an associated loss in the radiochemical reaction yield of the α-particle emitter labeled compound (e.g., a radiolabeled pharmaceutical or radiolabeled precursor). Radiochemical reaction yields of the α-particle emitter labeled compound will therefore generally be at least about 30%, typically at least about 50%, and often will be in the range from about 65% to about 95%. The radiochemical reaction yield is expressed as a percentage of the theoretical yield of the desired α-particle emitter labeled compound, based on the initial amounts of reactants and reaction stoichiometry, and considering the radioactive decay of the α-particle emitter over the course of the reaction. In general, the α-particle emitter will be the limiting reagent, so that the yield is determined based on the percentage the radioactivity of the desired product, relative to the total radioactivity added to the reaction.

Overall, stabilization of the α-particle emitter in an oxidant-containing solution will generally allow recovery of at least about 20% of the initial radioactivity of the α-particle emitter in the desired α-particle emitter labeled compound after reaction. That is, the initial radioactivity level of the α-particle emitter labeled compound is generally at least about 20%, typically from about 30% to about 80%, and often from about 35% to about 70%, of the initial α-particle emitter solution radioactivity level described above. This quantity depends on the extent of radioactive decay of the α-particle emitter during its storage time in solution. Importantly, however, this quantity is essentially independent of the radiation dose that the solution receives, during the time in which a stabilizing amount of oxidant is present in this solution. With respect to recovery of initial α-particle emitter radioactivity in the desired α-particle emitter labeled compound, a further advantage of using an oxidant-containing solution is a significant reduction in, and even the complete prevention of, losses of the α-particle emitter (e.g., $^{211}$At) due to evaporation or "leakage" during storage. This additional benefit was discovered, based on experimental observations of α-particle emitter volatilization in many $^{211}$At/methanol solutions, with and without oxidant. Besides preventing a direct loss of valuable α-particle emitter, storage in an oxidant-containing solution therefore also mitigates safety concerns associated with the emission of radioactive material into the environment.

As described above, storage of the α-particle emitter in an oxidant-containing solution vastly improves the yield of subsequent reactions involving the α-particle emitter. This allows for the shipment of compositions containing α-particle emitters, stabilized in solution containing an oxidant, to remote locations for the synthesis of radiolabeled compounds. In one embodiment, the α-particle emitter is stabilized for a period of at least about I hour prior to its use or reaction to form of a radiolabeled pharmaceutical or radiolabeled precursor. Stabilization according to the present invention is especially commercially advantageous for storage periods from about 3 hours to about 48 hours, during which time the α-particle emitter may be sent to virtually anywhere in the world. Typical storage periods for the stabilized α-particle emitter range from about 5 hours to about 24 hours, prior to use.

After storage of the α-particle emitter for a given period in an oxidant-containing solution, it can be used to prepare an α-particle emitter labeled compound either locally or at a remote location (e.g., a hospital) for administration to patients. In general, the use of a stabilizing amount of an oxidant maintains the α-particle emitter in a form (e.g., at an oxidation state) suitable for undergoing subsequent reactions to form α-particle emitter labeled compounds (i.e., a radiolabeled pharmaceutical or a radiolabeled precursor used to prepare it). Subsequent radiolabeling reactions may involve a number of possible mechanisms including electrophilic substitution, nucleophilic substitution, complexation, exchange, or metallic bonding. For example, the α-particle emitter $^{211}$At may be reacted with a compound having a reactive astatination site that is an electrophilic astatine substitution site, a nucleophilic astatine substitution site, an astatine complexation site, an astatine exchange site, or an astatine-metal bonding site.

Overall, the stabilized α-particle emitter of the present invention may be suitably employed in a wide range of subsequent radiolabeling reactions, as will be appreciated by those of skill in the art, having regard for the present disclosure. In some cases (e.g., nucleophilic substitution, discussed below), the stabilized α-particle emitter may be converted to an oxidation state that is more capable of undergoing a given radiolabeling reaction. In any event, stabilization according to the present invention affords minimal losses of the α-particle emitter (e.g., through volatilization during storage), high yields of radiolabeled pharmaceuticals and precursors, and high flexibility in terms of the types of subsequent reactions (some of which are discussed below) in which the α-particle emitter may be employed.

Suitable types of pharmaceuticals which may undergo radiolabeling with an α-particle emitter, for example, at an electrophilic substitution site, a nucleophilic substitution site, complexation site, exchange site, or metallic bonding site), or which may otherwise be modified with these types of reactive sites, include peptides and antibodies. For example, monoclonal antibodies such as IgG, through radiolabeling with an α-particle emitter, offer promise in the area of cancer therapy and treatment. Particular antitumor antibodies include those described, for example, in a recent review article. See Bast, R. C., Jr., Kousparou, C. A., Epenetos, A. A., Zalutsky, M. R., Kreitman, R. J., Sausville, E. A., and Frankel, A. E.: Antibodies. In: CANCER MEDICINE, $6^{th}$ edition. Kufe, D. W., Pollock, R. E., Weichselbaum, R. R., Bast, R. C., Jr., Gansler, T. S., Holland, J. F., and Frei III, E., eds., B. C. Decker, Hamilton, Ontario, 2003; 881-898.). Other types of agents having affinity for tumor cells and that may be radiolabeled with an α-particle emitter according to the present invention include thymidine analogues, peptide and nonpeptide receptor or transporter binding molecules, and metal complexes. Antibody fragments may also be radiolabeled using methods described herein.

In the case of electrophilic substitution (such as demetalation), the α-particle emitter (e.g., $^{211}At$) may be reacted with a number of possible substrates having one or more electrophilic substitution sites, to radiolabel these substrates. Such substrates include pharmaceuticals as well as pharmaceuticals that are modified to have an electrophilic substitution site and precursor compounds having an electrophilic substitution site. An electrophilic substitution site refers to an atom or moiety (e.g., an organometallic moiety such as —$Sn(C_4H_9)_3$) on the substrate that is capable of undergoing electrophilic attack by the α-particle emitter, resulting in replacement or substitution of the electrophilic substitution site with the α-particle emitter and, consequently, bonding of the α-particle emitter to the substrate. Electrophilic substitution sites are advantageously significantly more susceptible to electrophilic attack than potential surrounding sites (e.g., carbon-hydrogen bonds) on the substrate molecule. This property allows for regiospecific substitution with high yields, and often under mild reaction conditions. In the case where the halogen $^{211}At$ is used as the α-particle emitter, electrophilic substitution at an electrophilic astatination site may also be characterized as a halodemetalation reaction.

Precursors having an electrophilic substitution site for accepting the α-particle emitter can be used (i.e., reacted with the α-particle emitter to yield an intermediate) in the preparation of α-particle emitter labeled pharmaceuticals, based on their reactivity for coupling with (i.e., radiolabeling) a pharmaceutical. Typical classes of precursors include organometallic compounds having a metallic moiety which may be substituted by the α-particle emitter, together with an organic moiety that can couple with a pharmaceutical. Organic tin precursor compounds such as N-succinimidylalkylstannylbenzoates (e.g., N-succinimidyl 3-(tri-methylstannyl)benzoate or N-succinimidyl 3-(tri-n-butylstannyl)benzoate) are suitable. Electrophilic substitution involves replacement of the tin atom in these precursors with the α-particle emitter. For example, the electrophilic astatination of the precursors N-succinimidyl 3-(trimethylstannyl)benzoate (MeSTB) or N-succinimidyl 3-(tri-butylstannyl)benzoate (BuSTB) with $^{211}At$ yields N-succimidinyl-3-astatobenzoate (SAB) which is a key radiolabeled precursor used in the preparation of radiolabeled pharmaceuticals, such as radiolabeled monoclonal antibodies. Although they both generate radiolabeled SAB precursor, differences in the stability of the resulting leaving groups of these precursors (—$Sn(CH_3)_3$ and —$Sn(C_4H_9)_3$ in the case of MeSTB and BuSTB, respectively) contribute to some observed differences in their electrophilic astatination reactivity.

Other organometallic precursors having an electrophilic substitution site and an organic moiety for coupling with a pharmaceutical include other multi-valent metal compounds such as silanes that may be substituted with one or more organic moieties. Silane and other multi-valent metal compounds that are homologous to MeSTB and BuSTB, for example, may be used. These include, therefore, N-succinimidyl 3-(tri-methylsilyl)benzoate and N-succinimidyl 3-(tri-butylsilyl)benzoate. Particular homologues of these compounds are generated from the substitution of thallium, mercury, boron for tin or silicon, to provide compounds that likewise function as organometallic precursors. In addition to N-succimidyl benzoate, a number of other organic moieties may be joined to silicon or other multi-valent metal atoms, as would be recognized by those skilled in the art. These include alkyl-containing moieties (e.g., methyl groups), alkoxy-containing moieties (e.g., methoxy groups), ureido-containing moieties (e.g., ureidoalkyl groups), amino-containing moieties (e.g., aminoalkyl groups), sulfur-containing moieties (e.g., mercaptoalkyl groups), epoxy-containing moieties (e.g., glycidoxyalkyl groups), methacryl-containing moieties (e.g., methacryloxyalkyl groups), vinyl-containing moieties (e.g., vinylbenzylamino groups), haloalkyl-containing moieties (e.g., chloroalkyl groups), etc. Representative of the substituted tin- and silicon-containing precursors, therefore, are ureidopropyltrimethyltin, ureidopropyltrimethylsilane, aminopropyltrimethoxytin, aminopropyltrimethoxysilane, bis (triethyltinpropyl) tetrasulfide, bis (triethylsilylpropyl) tetrasulfide, mercaptopropyltrimethyltin, mercaptopropyltrimethylsilane, isocyanatopropyl triethyltin, isocyanatopropyl triethylsilane, and many others.

Nucleophilic substitution, complexation, exchange, or metallic bonding reactions may also be used in radiolabeling various substrates with the stabilized α-particle emitter. Substrates capable of undergoing such reactions include pharmaceuticals having, as well as pharmaceuticals that are modified to have, a nucleophilic substitution site, complexation site, exchange site, or metallic bonding site and precursor compounds having a nucleophilic substitution site, complexation site, exchange site, or metallic bonding site.

Nucleophilic substitution reactions between the α-particle emitter and substrate (e.g., an organic molecule which may be aromatic or aliphatic) may proceed via relatively simple unimolecular ($S_N1$) or bimolecular ($S_N2$) pathways. As is known in the art, $S_N1$ reactions proceed through the formation of a carbocation. Also, $S_N2$ pathways are stereospecific. The α-particle emitter $^{211}At$, for example, in its radiohalide form, can serve as the attacking reagent in an $S_N^2$ reaction, with a nucleophilicity (relative to other halogens) that depends on the on the solvent proticity. In addition to nucleophilicity, reaction yields are determined by a number of other kinetic parameters (e.g., leaving group stability and electronic interactions) and thermicity.

Nucleophilic substitution reactions include those which are analogous to known radioiodination reactions, but with the α-particle emitter used in place of iodine. Nucleophilic substitution may also involve the replacement of iodine in the substrate molecule with astatine in both homogeneous and heterogeneous systems. For example, yields of up to 99% have been reported for the replacement of I with At in benzene in homogenous halobenzene/butylamine systems. This and other examples are found in Coenen H., et al., RADIOCHIMICA ACTA 34:47-68 (1989); Vasaros L., et al., RADIOCHIMICA ACTA 47:119-128 (1989); Berei K., et al., *Recent Advances in the Organic Chemistry of Astatine*, Budapest, Hungary: KFKI ATOMIC ENERGY RESEARCH INSTITUTE (1994); Report KFKI-1994-4/J,K.

Representative radiolabeling reactions involving nucleophilic substitution include the labeling of elastin-like polypeptides (ELPs). ELPs are biopolymers which undergo a reversible phase transition, leading to aggregation/precipitation at the site of the tumor, when local hyperthermia is induced. In one embodiment of the invention, the α-particle emitter, after storage in an oxidant-containing solution, is reacted with a compound having a nucleophilic substitution site to provide the α-particle emitter labeled compound. Prior to this reaction, it may be desirable to add a reducing agent (e.g., sodium bisulfite) to the solution. This can conveniently convert the α-particle emitter (e.g., after storage in an oxidized form) into a reduced form (e.g., astatide) that is a more effective nucleophile.

Complexation reactions may also be used for radiolabeling various substrates with the stabilized α-particle emitter. Complexation refers to reactions of the α-particle emitter with a ligand functional group such as those present in chelating agents. Generally, the more covalent the bond character is between the α-particle emitter and the ligand, the more stable the resulting complex is. Different oxidation states of the α-particle emitter therefore lead to different complex stabilities. Chelating agents include resins having sulfur atom-bearing functional groups, such as thiosemicarbazide and its derivatives, which may be incorporated, for example, into styrene-divinylbenzene copolymers or ion exchange resins such as the weakly acidic Amberlite IRC-50® (Rohm and Haas Company, Philadelphia, Pa. USA). In the latter case, the resulting polymer contains a multidentate chelate ring containing O, N, and S donor sites.

A representative thiosemicarbazide derivative functional group is diacetyl-bis(N-methylthiosemicarbazone), which, for example has been found to complex with copper at varying oxidation states. Both aromatic (e.g. 4-phenylthiosemicarbazide) and aliphatic (e.g., 4-methylthiosemicarbazide) thiosemicarbazide functional groups may serve as complexation sites. The use of chelating resins discussed above in complexation reactions is described, for example, by Kamalika, R. et al., APPLIED RADIATION AND ISOTOPES 60:793-799 (2004); Sugii, A. et al., TALANTA 31:1079 (1984); and Siddhanta, S. et al., TALANTA 32:457 (1985). The α-particle emitter $^{211}$At, while a halogen, is the heaviest element in this group and therefore the least electronegative. It is contemplated therefore that $^{211}$At may exhibit electropositive (or even metallic) properties, making it amenable to the complexation reactions described above.

The chelating agents discussed above and other compounds having a complexation site may therefore serve as a precursor which can be labeled with an α-particle emitter. The resulting intermediate can then be coupled to another molecule (e.g., a pharmaceutical such as an antibody, protein, or peptide) to form a radiolabeled pharmaceutical. In one embodiment of the invention, therefore, the α-particle emitter, after storage in an oxidant-containing solution, is reacted with a compound having a complexation site to provide the α-particle emitter labeled compound. The compound having the complexation site may therefore be a precursor (and the α-particle emitter labeled compound may be an intermediate) in the preparation of the radiolabeled pharmaceutical.

Exchange reactions may also be used to radiolabel pharmaceuticals and precursors with the stabilized α-particle emitter. These reactions involve direct attack by the α-particle emitter of a carbon-hydrogen bond, rather than an organometallic bond (e.g., a carbon-metal) bond, as in the case of certain electrophilic substitution (such as demetalation) reactions described above. The use of an exchange reaction in the preparation of a radiolabeled compound may be advantageous in that it does not necessarily require modification or derivatization of a pharmaceutical or precursor with, for example, an organometallic moiety. Product contamination with metals (e.g., tin) used for this modification or derivatization is also avoided. Exchange reactions generally proceed under mild reaction conditions and through the positive polarization of the α-particle emitter with an electron withdrawing group. As stated above, the α-particle emitter $^{211}$At may become positively polarized and therefore capable of direct electrophilic halogenation of a substrate. Metallic α-particle emitters may similarly undergo such exchange reactions.

Metallic bonding as a means for radiolabeling pharmaceuticals or precursors involves the direct interaction and binding of α-particle emitter, subsequent to stabilization according to the present invention, with a metal a metallic binding site. Examples, in the case of the α-particle emitter $^{211}$At, include the reaction at an astatine-metal binding site to form an astatine-tellurium colloid. See Bloomer, W. D., et al., INT. J. RADIAT. ONCOL. BIOL. PHYS. 10:341-348 (1984). Binding to metal-containing (e.g., gold-containing) nanoparticles, represents another type metallic bonding reaction that may be used for radiolabeling with the stabilized α-particle emitter.

Precursors described above (e.g., an organometallic compound having an electrophilic substitution site) may be used in the synthesis of pharmaceuticals that are radiolabeled with an α-particle emitter. In accordance with the present invention, the α-particle emitter is stabilized in a solution containing an oxidant. The stabilized α-particle emitter may subsequently be reacted with a precursor to label it with the α-particle emitter. Most, if not all, of the solution may be evaporated prior to coupling the desired pharmaceutical with the α-particle emitter labeled precursor, which serves as an intermediate in the ultimate preparation of the radiolabeled pharmaceutical. Because stabilization of the α-particle emitter with an oxidant allows the preparation of radiolabeled pharmaceuticals having therapeutically effective levels of radioactivity, such radiolabeled pharmaceuticals (e.g., radiolabeled antibodies) may be administered to patients in clinical applications such as in the inhibition of tumor cell growth and/or in the treatment of cancer. Radiolabeled pharmaceuticals for such uses generally will require an initial level or radioactivity (i.e., immediately after the pharmaceutical is radiolabeled) of at least about 5 mCi (185 MBq), typically from about 10 mCi (370 MBq) to about 50 mCi (1.9 GBq), and often from about 15 mCi (560 MBq) to about 40 mCi (1.5 GBq). These levels of radioactivity for α-particle emitter labeled pharmaceuticals are now possible through stabilization of the α-particle emitter according to the present invention.

Because of the storage stability achieved using an oxidant-containing solution, α-particle emitters can be provided to (shipped, transported, sent), and used in, remote locations for the synthesis of α-particle emitter labeled compounds. This synthesis may occur hours or even days after the stabilized composition containing the α-particle emitter is prepared. Simple kits, comprising two compositions in separate compartments or containers (e.g., separate vials), may be used to prepare α-particle emitter labeled compounds. The first composition is a stabilized composition comprising the α-particle emitter in a solution containing an oxidant. Advantageously, this composition may be contained effectively free of (e.g., in the absence of) the compound having any of the reactive sites described above (e.g., a reactive astatination site), with which the α-particle emitter subsequently reacts (i.e., upon combining the first composition with a second composition). "Effectively free" refers to compounds having a reactive site being present in the stabilized composition in an amount of less than about 10% by weight, generally less than about 1% by weight, and typically less than about 0.1% by weight. In one embodiment, the stabilized composition contains the α-particle emitter and an oxidant-containing solution (e.g., an alcohol and an oxidant), in the absence of any other components in quantities that would materially affect its basic and novel characteristics.

The second composition used in kits of the present invention comprises the compound, as described above (e.g., MeSTB or BuSTB), having a reactive site as described above (e.g., a reactive astatination site). After an initial period of storing the α-particle emitter in the stabilized composition (e.g., for several hours, as may be required for shipment to a remote location), the first and second compositions are combined to react the α-particle emitter with the compound having a reactive site, thereby generating an α-particle emitter labeled pharmaceutical (e.g., an α-particle emitter labeled monoclonal antibody) or an α-particle emitter labeled precursor (e.g., α-particle emitter labeled SAB).

Overall, the use of an oxidant-containing solution for the stabilization of α-particle emitters allows for their subsequent reactions (e.g. electrophilic substitution) to proceed with high yields of the desired α-particle emitter labeled compounds. The generation of unwanted side products is reduced or avoided throughout the synthesis steps used to ultimately prepare the α-particle emitter labeled pharmaceutical, to be administered therapeutically. This results in improved product purity and a reduction in the loss of valuable reagents.

All references cited in this specification, including without limitation, all U.S., international, and foreign patents and patent applications, as well as all abstracts and papers (e.g., journal articles, periodicals, etc.), are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references. In view of the above, it will be seen that several advantages of the invention are achieved and other advantageous results obtained.

As various changes could be made in the above methods and compositions without departing from the scope of the invention, it is intended that all matter contained in this application, including all theoretical mechanisms and/or modes of interaction described above, shall be interpreted as illustrative only and not limiting in any way the scope of the appended claims.

The following examples are set forth as representative of the present invention. These examples are not to be construed as limiting the scope of the invention as these and other equivalent embodiments will be apparent in view of the present disclosure and appended claims.

Materials and Methods

Many of the experimental details are referenced in previous papers. See Pozzi, O. et al., J Nucl Med. 46:1393-1400 (2005) and Pozzi, O. et al., J Nucl Med. 46:700-706 (2005). Studies were performed with N-succinimidyl 3-(tri-methylstannyl)benzoate (MeSTB) and N-succinimidyl 3-(tri-n-butylstannyl)benzoate (BuSTB), used in the synthesis of radiolabeled N-succimidinyl-3-astatobenzoate (SAB) and initially prepared as described in Zalutsky, M. et al., Int J Rad Appl Instrum[A] 38:1051-1055 (1987) and Garg, P. K. et al., Int Rad Appl Instrum[A] 40:485-490 (1989). MeSTB and BuSTB purity was confirmed by TLC before each experiment. All solvents were reagent grade or better and used as purchased.

Analyses were performed using reverse phase HPLC on a Beckman System Gold HPLC equipped with a diode array detector and a radioscope detector. A Waters Xterra 4.6×250 mm (10 μm) column was used. The elution was made with a gradient of solvent B (acetonitrile/water/acetic acid (95/5/0.1, w/w/w)) in solvent A (water/acetic acid 0.1 wt-%) held at 48% of B for 13 min followed by 48% to 100% linear gradient of B over 2 min, followed by 100% solvent B up to the end of the HPLC run. The flow was 1 mL/min increased from 1 to 1.5 mL/min between 15-15.5 min and held until the end of the chromatography run. The UV signal at both 220 nm and 254 nm, as well as the radioactive signal were monitored. Aliquots of 50 μL were used for HPLC analysis except for longer exposure times (~24 h) and when the initial radioactivity level was low; in these cases, aliquots >50 μL were used. Samples were injected on the HPLC immediately after they were obtained. In all experiments, authenticated standards of 3-iodobenzoic acid (IBA) and N-succinimidyl 3-iodobenzoate (SIB) were also run for comparison.

The $^{211}$At was produced at the Duke University Medical Center cyclotron and purified by dry distillation as described in Larsen, R. H. et al., Appl Radiat Isotop. 47:135-143 (1996). Radioactivity levels of $^{211}$At-containing samples were measured using a CRC-7 dose calibrator (Capintec, Pittsburgh, Pa.). All of the α-particle and α-recoil nuclei decay energy was assumed to be deposited in the $^{211}$At-containing solutions because of the short range of these emissions relative to the dimensions of the reaction mixtures. Uniform distribution of the reactants in the solvent also was assumed. The absorbed dose was therefore calculated as described previously.

EXAMPLE 1

Generation of Two Forms of the α-Particle Emitter, $^{211}$At in Methanol

Figure 1A:
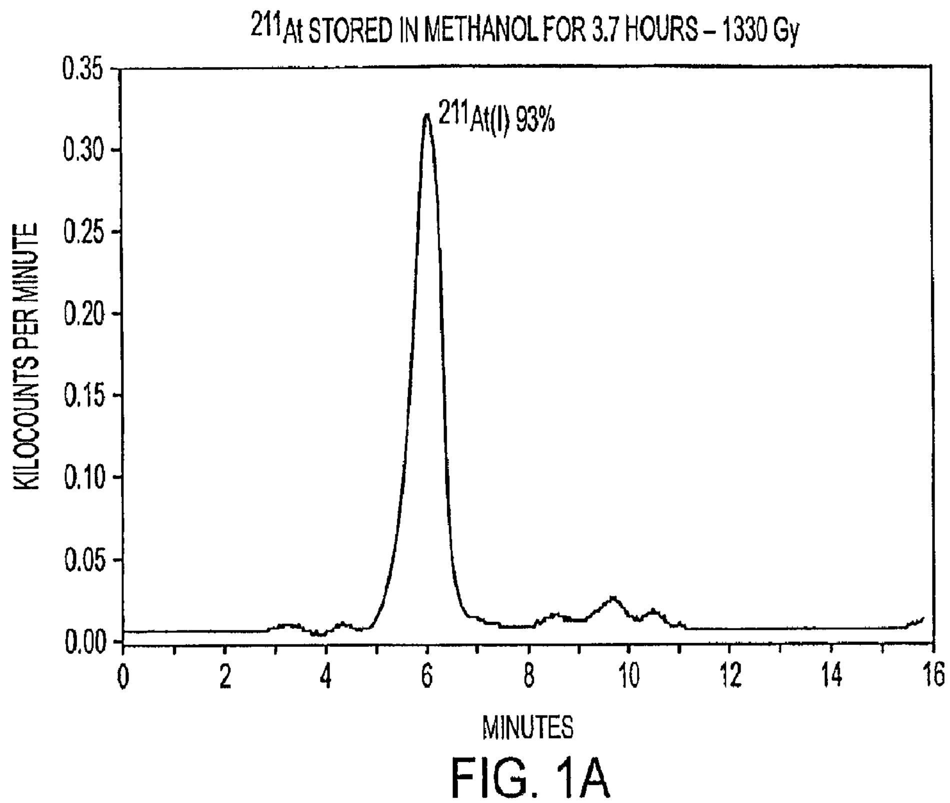
FIG. 1 shows HPLC chromatograms of $^{211}$At, stored in methanol for periods of 3.7 hours and 21.5 hours. These storage times resulted in calculated radiation doses of 1,330 Gy and 3,630 Gy, respectively, received by the methanol.
Figure 1B:
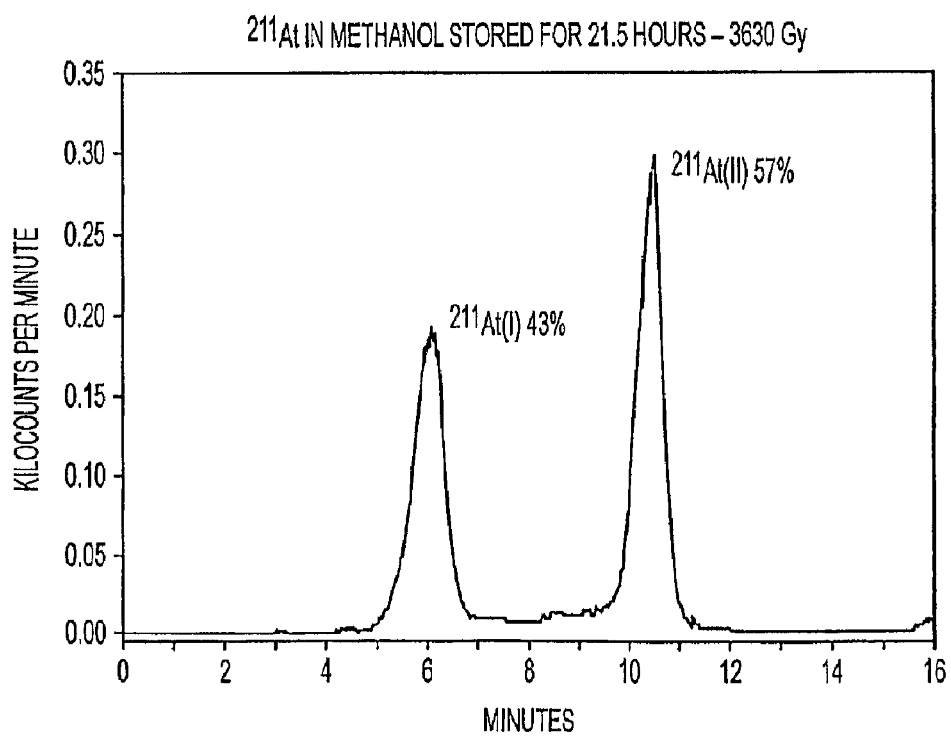

A sample of $^{211}$At was prepared by cyclotron bombardment of $^{209}$Bi, volatilized from this target, and eluted in methanol. The sample was divided into two separate vials. The vials were then stored for periods of 3.7 and 21.5 hours, in order to evaluate the effect of the different resulting radiation doses on the form of the $^{211}$At. After these storage periods, which resulted in calculated radiation doses to the methanol of 1,330 Gy and 3,630 Gy, respectively, HPLC analyses were performed on aliquots from the two vials. The chromatograms are shown in FIG. 1.

At the higher radiation dose after 21.5 hours, the $^{211}$At radioactivity was divided essentially between two peaks (i.e., two different forms of astatine), referred to hereinafter as At(I) and At(II). The first peak (observed at the lower retention time) corresponded to that observed for freshly-prepared $^{211}$At. As discussed below, this form, At(I), was found to be reactive in the synthesis of N-succinimidyl 3-[$^{211}$At]astatobenzoate (SAB). The second peak corresponded to another form of astatine which appeared to be generated radiolytically (i.e., as the result of irradiation of the methanol). As discussed below, this form, At(II), was found to be considerably less reactive that At(I) in the synthesis of N-succinimidyl 3-[$^{211}$At]astatobenzoate (SAB).

EXAMPLE 2

The Effect of pH on the Relative Amounts of $^{211}$At Forms Generated

Figure 2A:
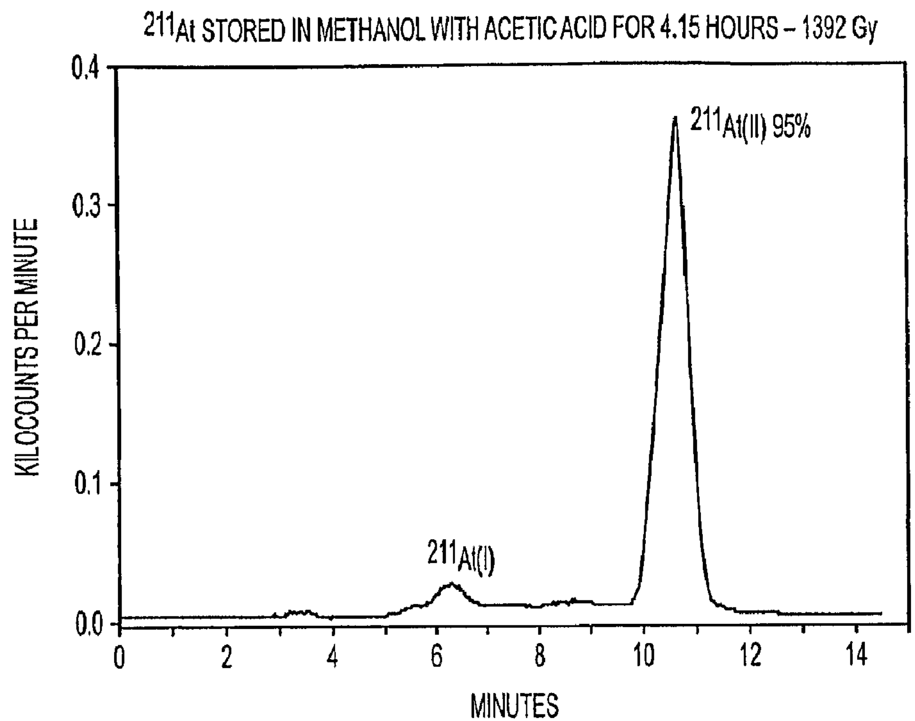
FIG. 2 shows HPLC chromatograms of $^{211}$At, stored in methanol/acetic acid for periods of 4.15 hours and 21.9 hours. These storage times resulted in calculated radiation doses of 1,392 Gy and 3,520 Gy, respectively, received by the methanol/acetic acid.
Figure 2B:
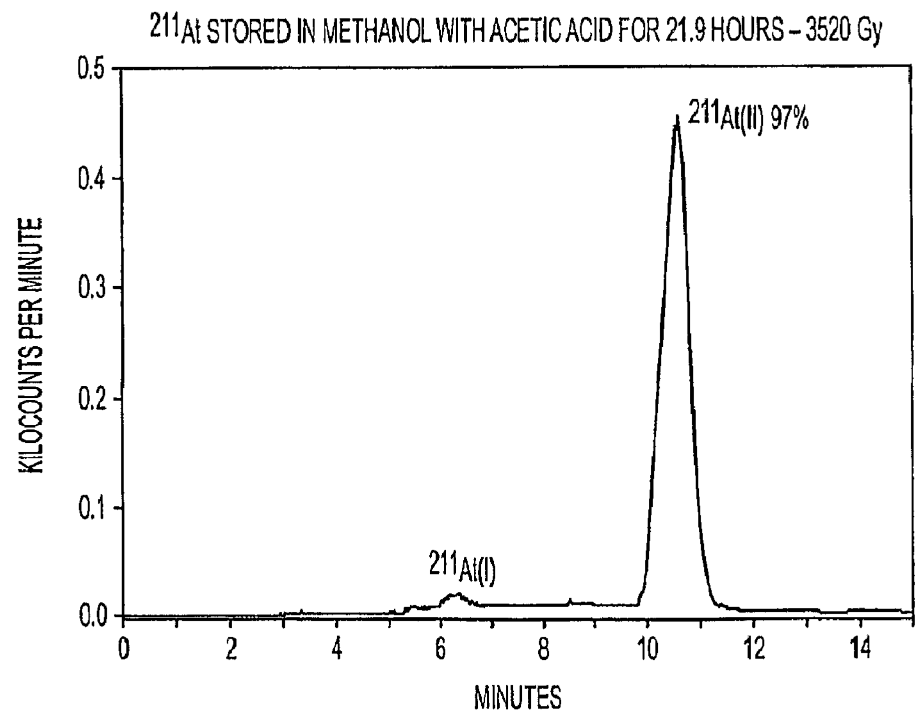

Two additional vials of $^{211}$At in methanol were prepared from the same $^{211}$At synthesis in Example 1. These vials were likewise stored for 4.15 and 21.9 hours prior to HPLC analysis, such that the calculated radiation doses to the methanol were 1,392 Gy and 3,520 Gy, respectively. The pH of the solution was significantly lowered during the storage period, however, using acetic acid. HPLC analyses were performed on aliquots from the two vials, and the chromatograms are shown in FIG. 2.

Even at the relatively low dose of 1,392 Gy, the reduction in pH of the solution, due to the presence of acetic acid, resulted in essentially all of the astatine being converted to the At(II) form (observed at the higher retention time). This conclusion was based on a comparison between HPLC chromatogram peaks in Example 2, relative to those in Example 1 where the $^{211}$At was stored in solution at neutral pH. It was believed that low pH values enhanced the radiolytic generation of reducing species, which ultimately converted At(I) to At(II).

EXAMPLE 3

Figure 3:
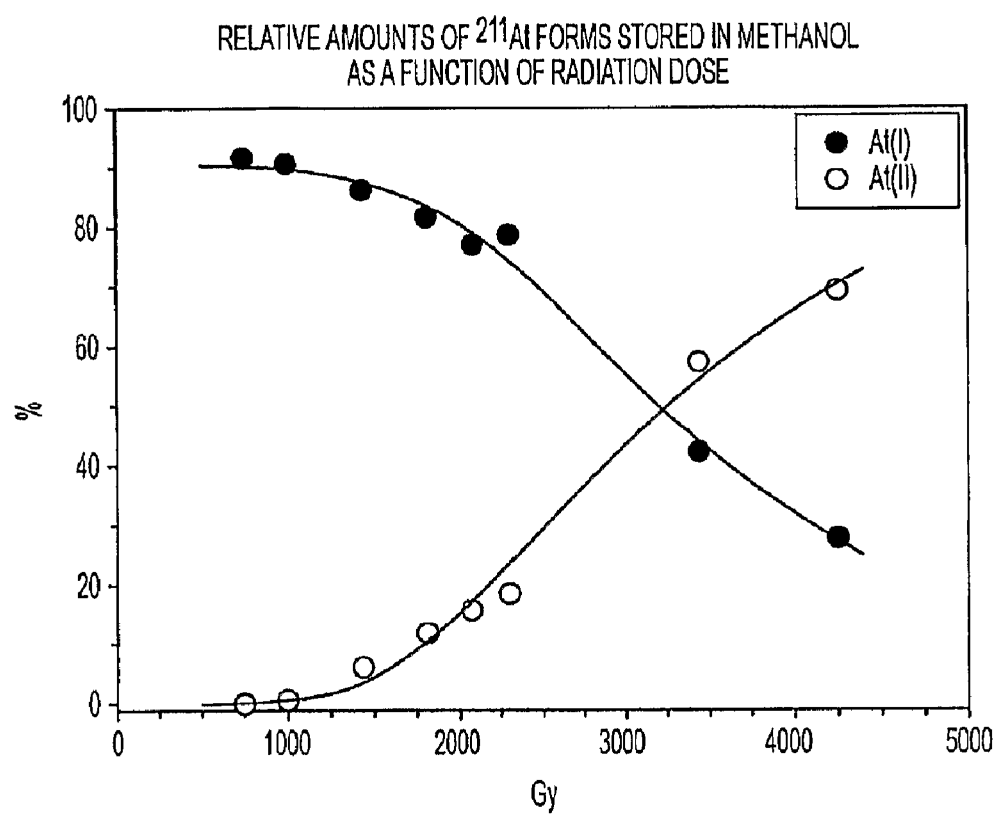
FIG. 3 shows the relationship between the relative amounts of astatine forms stored in methanol as a function of radiation dose.

The Effect of Radiation Dose on the Relative Amounts of $^{211}$At Forms Generated A $^{211}$At solution in methanol was prepared as in Example 1. Aliquots taken at successive time periods, corresponding to increasing calculated alpha-particle radiation dose levels, were analyzed using HPLC. FIG. 3 shows the relationship between the amounts of the astatine forms At(I) and At(II) forms generated, as a function of radiation dose. The $^{211}$At form clearly depended on the amount of radiation received by the methanol.

It was believed that the conversion from At(I) to At(II) resulted from the radiolytic generation of reducing species in the methanol, and that the At(II) form of astatine observed at the longer HPLC retention time was a reduced form of astatine.

EXAMPLE 4

Characterization of the At(II) Form Observed at the Longer HPLC Retention Time

Figure 4A:
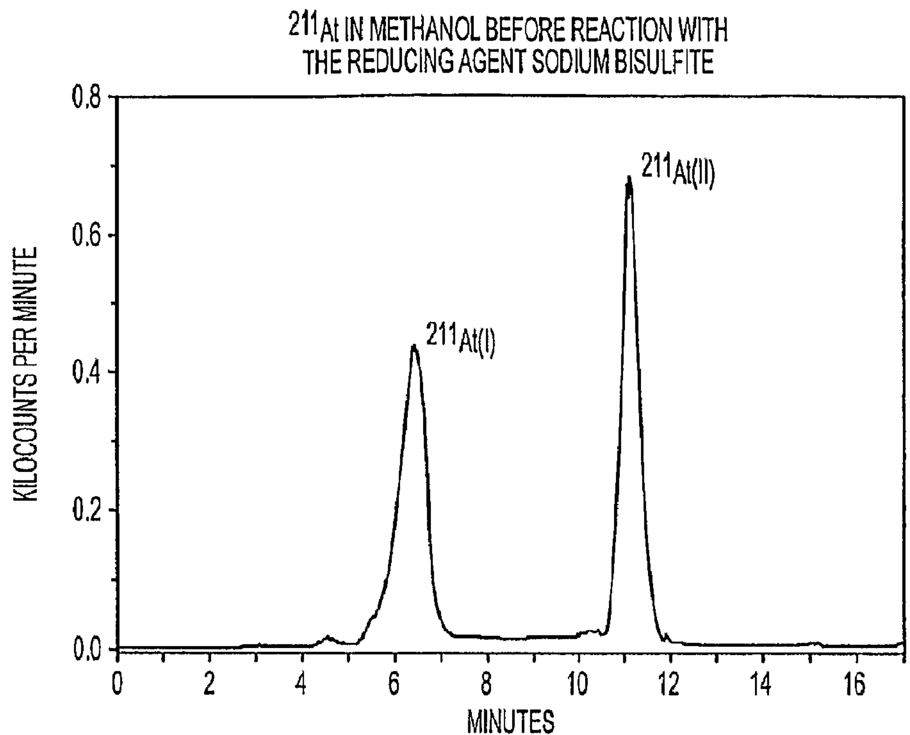
FIG. 4 shows HPLC chromatograms of $^{211}$At in methanol, both before and after reaction with the reducing agent sodium bisulfite.
Figure 4B:
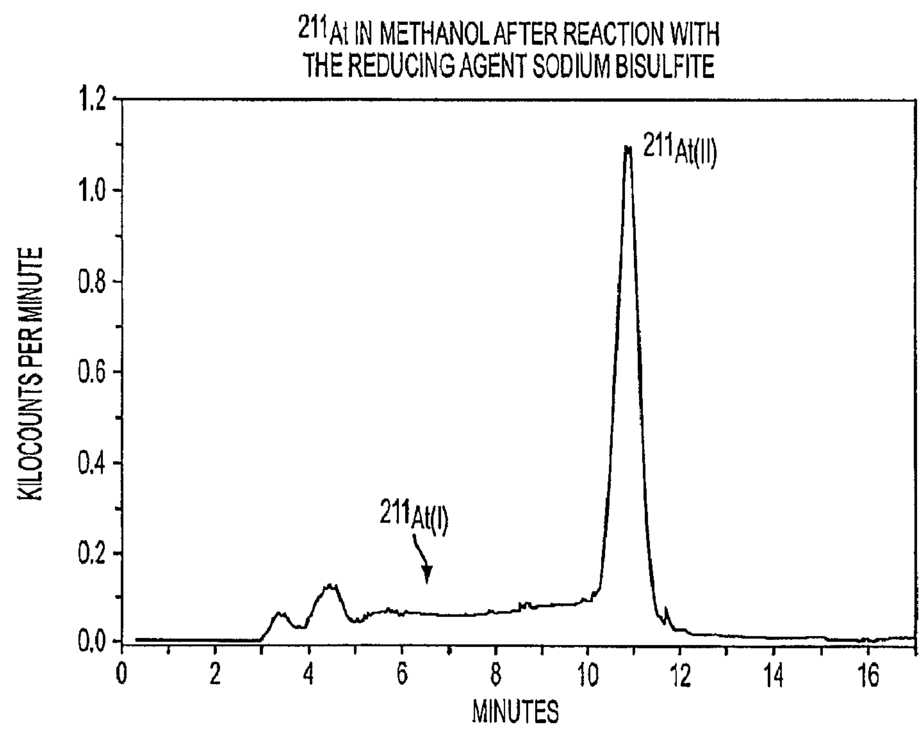

A $^{211}$At solution in 460 microliters (μL) of methanol was prepared as in Example 1. A 30 μL aliquot of this solution, having 25 μCi (925 kBq) of initial radioactivity, was combined with 30 μL of the known reducing agent sodium bisulfite (2 μmoles). The sodium bisulfite was allowed to react for 30 minutes. HPLC chromatograms were generated for aliquots of the $^{211}$At in methanol, both prior to and after the reaction with sodium bisulfite. Approximately equal levels of radioactivity were injected into the HPLC by adjusting the volume of the two aliquots used. The HPLC chromatograms of aliquots of these astatine solutions before and after the sodium bisulfite reaction are shown in FIG. 4.

The astatine in methanol was converted almost entirely to the form having a retention time corresponding to At(II), as a result of reaction with the known reducing agent, sodium bisulfite. This provided further evidence that the At(II) form of astatine observed at the longer HPLC retention time was a reduced form of astatine.

EXAMPLE 5

Reactivity of At(I) and At(II) for Electrophilic Astatination (with NCS in the Reaction Mixture)

Figure 5:
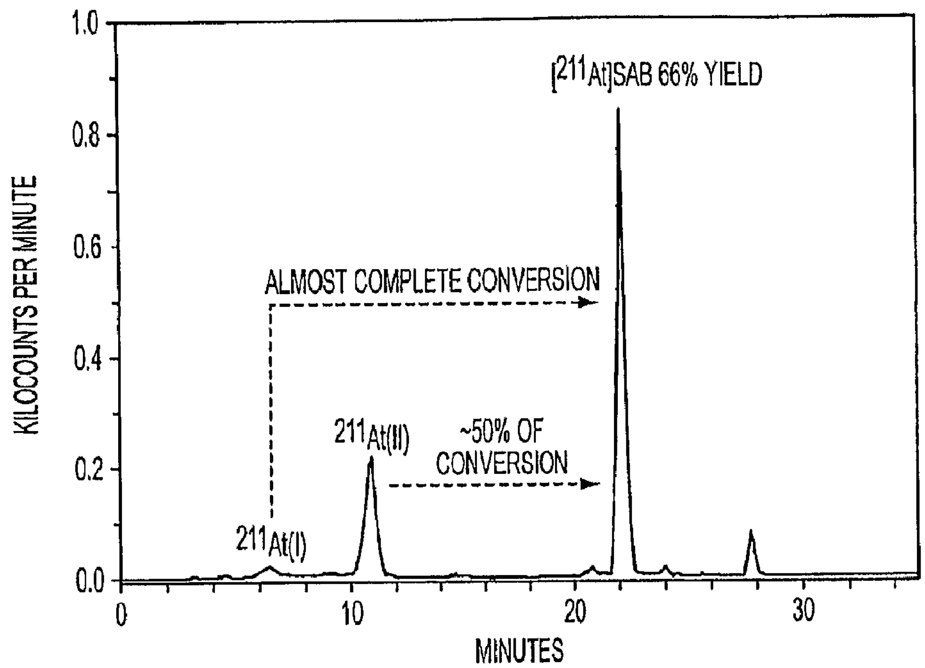
FIG. 5 shows HPLC chromatograms of acidic and neutral reaction product solutions, after the electrophilic astatination of N-succinimidyl 3-(tri-n-butylstannyl)benzoate (BuSTB) with $^{211}$At, stored in methanol, to form N-succimidinyl-3-[$^{211}$At]astatobenzoate (SAB).
Figure 5:
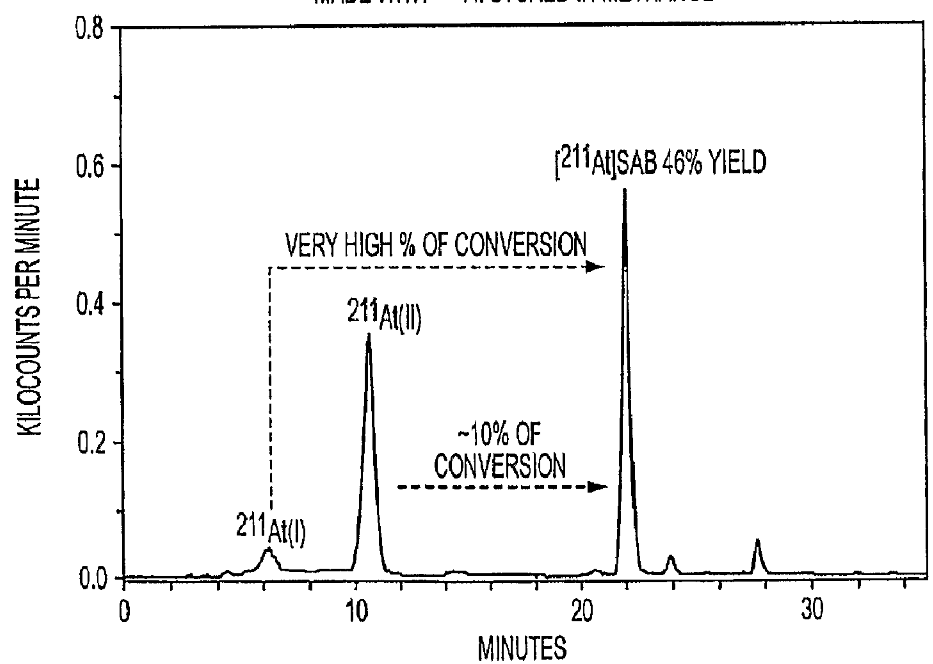

Two samples, 200 μL each, of the $^{211}$At in methanol prepared in Example 4 were used in the synthesis of the radiolabeled precursor N-succimidinyl-3-[$^{211}$At]astatobenzoate (SAB) via electrophilic astatination. The $^{211}$At in methanol solutions were each poured into vials containing 80 μg of N-succinimidyl 3-(tri-n-butylstannyl)benzoate (BuSTB), and 200 μg of N-chlorosuccinimide (NCS) in 100 μl of methanol were added to each of these vials. These reaction mixtures were identical, except that the first reaction was performed under acidic conditions through the addition of 12 μl of acetic acid. The reaction mixtures were shaken for 20 minutes, and 50 μl aliquots were removed for HPLC analysis. The HPLC chromatograms of these reaction product solutions, under both acidic and neutral conditions, are shown in FIG. 5.

Based on the HPLC chromatograms, the almost complete disappearance of the peak corresponding to At(I) indicated that this astatine form is highly reactive for electrophilic astatination. In contrast, a significant portion of At(II) remained, indicating that this astatine form was considerably less reactive in the synthesis of SAB. Also, the At(II) that had already formed prior to the SAB reaction, as a result of the radiation dose which the methanol received during storage, was not effectively oxidized to At(I) by the presence of the oxidant NCS during the electrophilic astatination reaction. That is, the formation of At(II) due to radiolytic effects is not easily reversed. Notwithstanding, a greater portion of the At(II) was apparently converted to SAB under acidic versus neutral reaction conditions (about 50% versus about 10% At(II) conversion, respectively), with NCS in the reaction mixture.

EXAMPLE 6

Radiation Dose (and At(II) Amount) Versus SAB Yield (No NCS in the Reaction Mixture)

Figure 6:
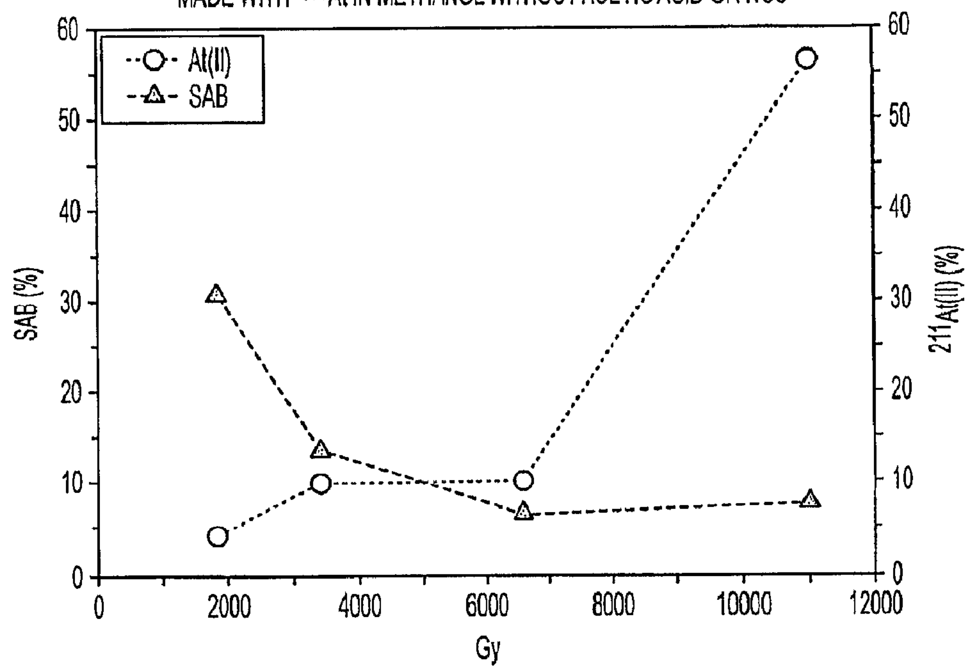

Multiple electrophilic astatination reactions of $^{211}$At with BuSTB to form the radiolabeled precursor SAB, were carried out as described in Example 5, but without the addition of acetic acid (i.e., at neutral pH) or NCS. The $^{211}$At in methanol solutions varied with respect to their storage times and therefore the radiation doses received. Aliquots of the reaction mixtures obtained after the reaction of the $^{211}$At to form SAB were analyzed by HPLC to determine the At(II) amount and SAB yield as a function of the radiation dose which the $^{211}$At in methanol received. These results are shown in FIG. 6.

The inverse relationship between the SAB yield and the amount of At(II) present in the reaction mixture further showed that the astatine form designated At(II) was far less reactive for SAB synthesis than the astatine form designated At(I).

EXAMPLE 7

Effect of Reaction Mixture pH on SAB Yield (with NCS in Reaction Mixture)

Figure 7A:
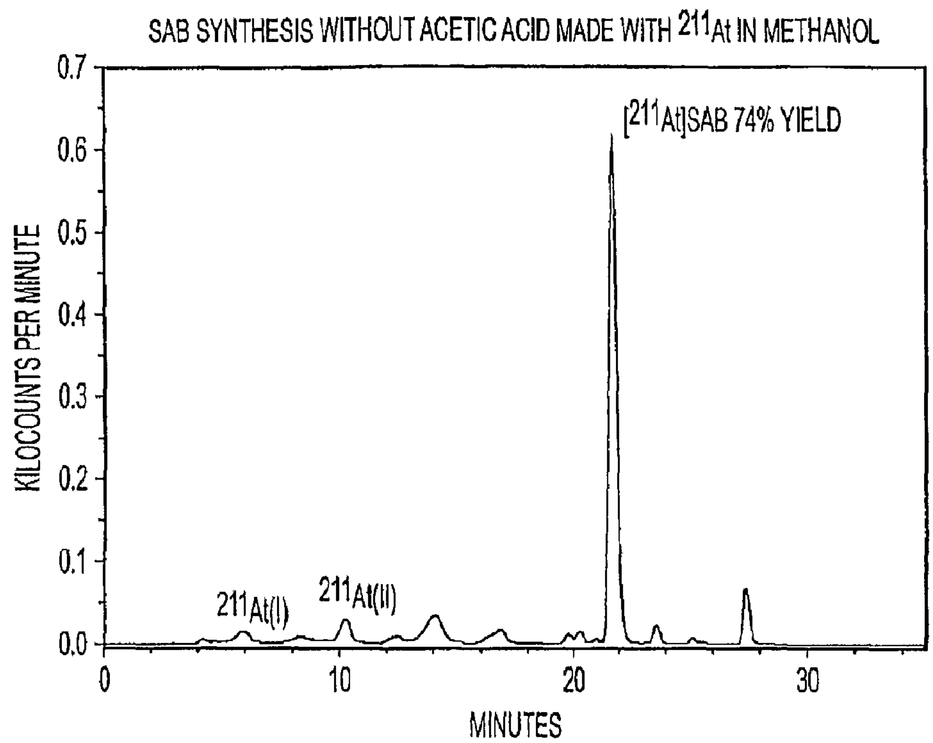
FIG. 7 shows additional HPLC chromatograms of acidic and neutral reaction product solutions, after the electrophilic astatination of BuSTB with $^{211}$At, stored in methanol, to form SAB.
Figure 7B:
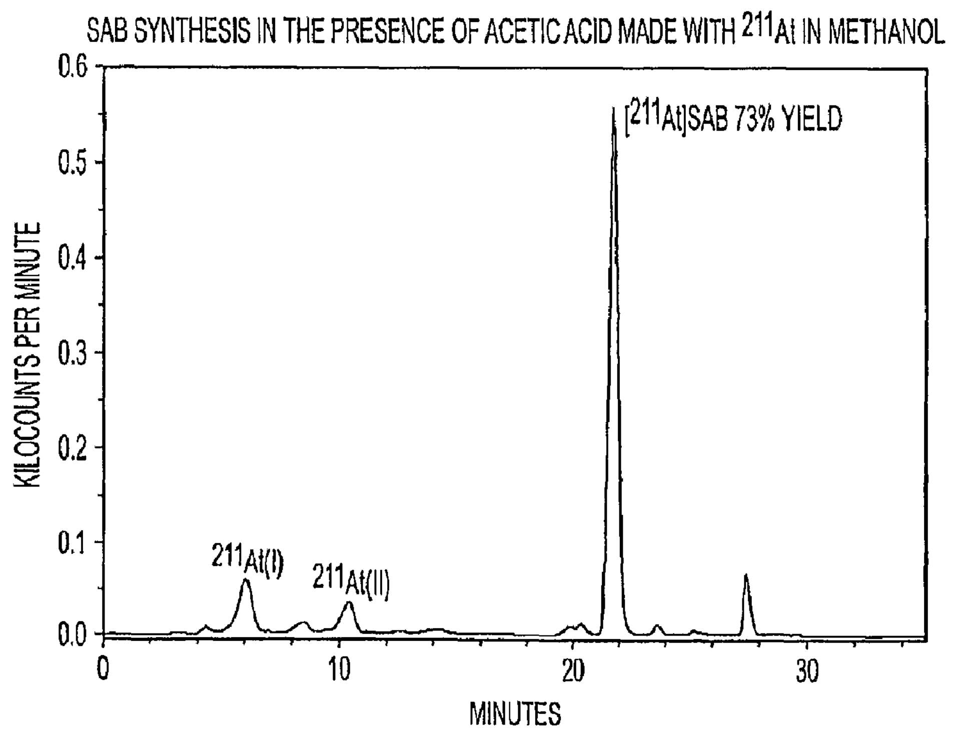

Electrophilic astatination reactions of two samples of $^{211}$At with BuSTB, to form the radiolabeled precursor SAB, were carried out as described in Example 5. However, compared to Example 5, the radiation dose that the methanol solution, containing the $^{211}$At, received prior to reaction was less. One reaction mixture was made acidic by the addition of acetic acid. The HPLC chromatograms for aliquots of the acidic and neutral reaction product solutions are shown in FIG. 7.

The SAB yields were essentially the same for electrophilic astatination reactions run under acidic (73% yield) and neutral (74% yield) conditions. Relative to Example 5, the higher SAB yields in this experiment resulted from a lower radiation dose that the $^{211}$At in methanol received, prior to the reaction. That is, relatively less of the astatine form designated At(II) was present in the reaction mixture.

Based on the results of Examples 5 and 7, an acidic reaction environment may benefit the SAB yield when NCS is present. Previous experiments, however, showed that acidic conditions in the absence of NCS were detrimental to SAB yield. Pozzi, O. et al., J NUCL MED. 46:1393-1400 (2005). This was believed to result from reducing species generated by radiolysis of the acidic reaction environment. The use of NCS therefore appeared to protect from, or even partly reverse, these adverse effects, leading to the conversion of At(I) to At(II), the latter form being relatively less reactive for electrophilic astatination.

EXAMPLE 8

Stabilization of the Reactive Astatine Form At(I) Using NCS

Figure 8A:
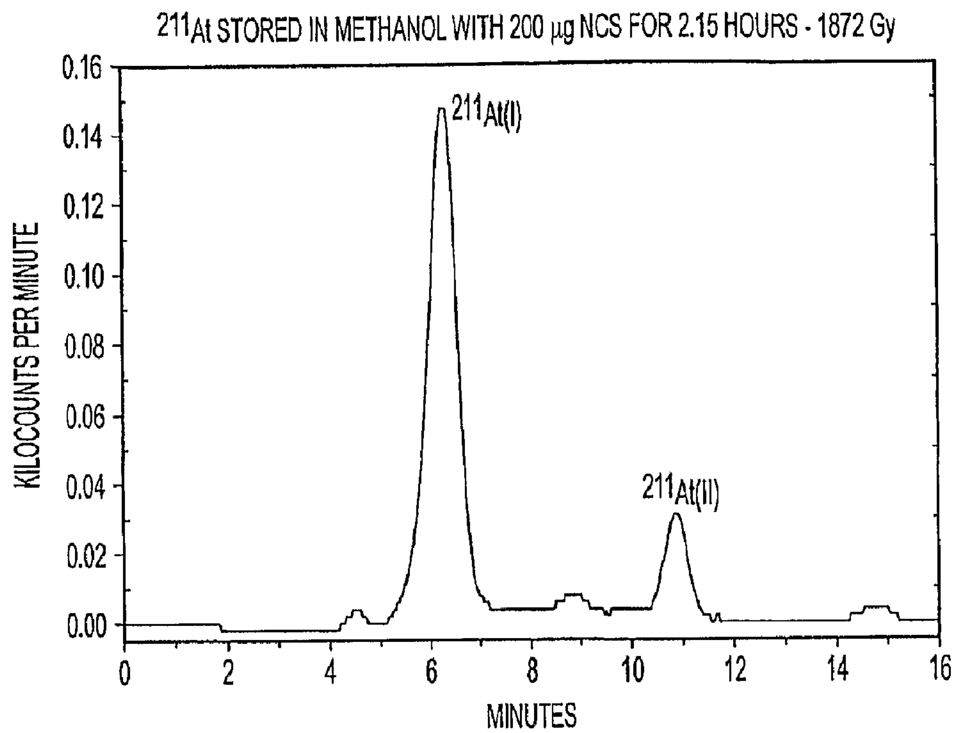
FIG. 8 shows HPLC chromatograms of $^{211}$At in methanol that was stabilized with 200 μg of N-chlorosuccinimide (NCS) shortly after its preparation. The chromatograms were obtained after storage for periods of 2.15 hours and 25.6 hours, such that the calculated radiation doses received by the NCS-containing methanol, were 1,872 Gy and 7,961 Gy, respectively.
Figure 8B:
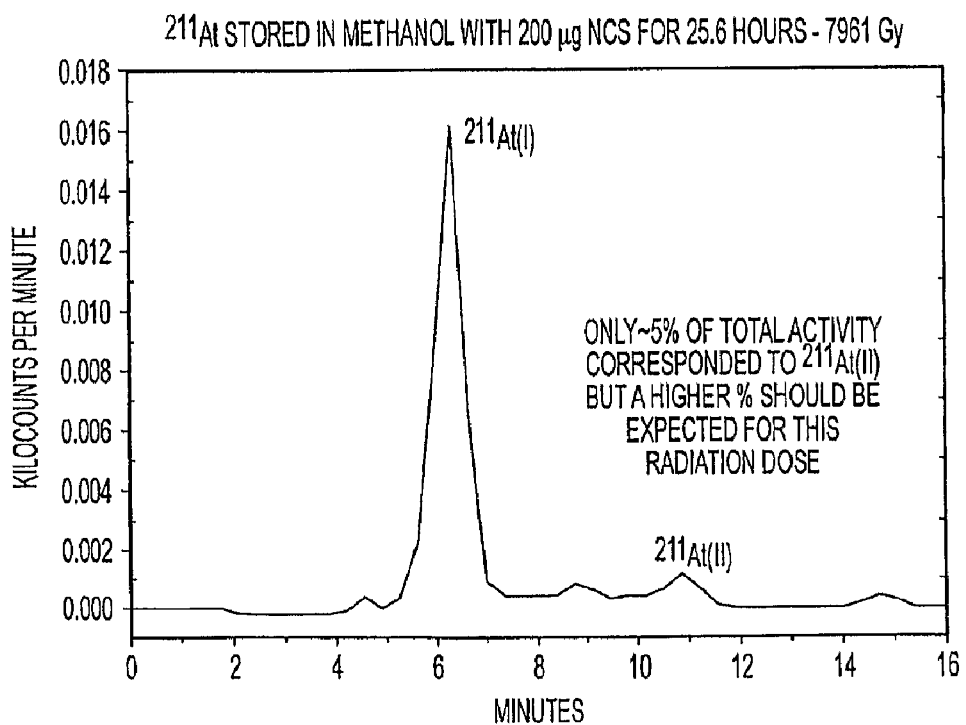

A 200 μl sample of $^{211}$At was prepared and eluted in methanol as described in Example 1. Shortly after this elution, 200 μg of NCS was added. Aliquots of the sample were analyzed by HPLC after 2.15 hours and again after 25.6 hours of storage (or "aging"), at which times the methanol received calculated radiation doses of 1,872 Gy and 7,961 Gy, respectively. Based on Example 1, these radiation doses would have been expected to convert a substantial portion of the initially present At(I) into At(II). The HPLC chromatograms from this experiment are shown in FIG. 8.

Protection (or stabilization) of the $^{211}$At in methanol with 200 μg of NCS resulted in only 5% of the measured astatine radioactivity in the peak corresponding to the form At(II), even after the methanol received a calculated radiation dose of 7,961 Gy. Compared to the results obtained in Example 1, where a radiation dose of only 3,630 Gy resulted in 57% conversion of At(I) to At(II), the addition of only 200 μg of NCS to 200 μl of $^{211}$At in methanol effectively stabilized almost all of the astatine in its reactive At(I) form.

EXAMPLE 9

Reactivity of the Stabilized Astatine for Electrophilic Astatination

The sample of $^{211}$At in methanol prepared in Example 8, which was stabilized in NCS and stored for 25.95 hours, was used in the synthesis of SAB, according to the procedures in Example 5. A second sample containing $^{211}$At eluted in methanol, was stabilized with NCS at the same time for 23.8 hours, but using 2,100 μg rather than 200 μg. The HPLC chromatograms of the reaction product solutions after having received a radiation dose of nearly 8,000 Gy in each case, are shown in FIG. 9.

Based on the HPLC chromatograms, the use of NCS in both the 2,100 μg and 200 μg amounts stabilized the $^{211}$At reactivity for electrophilic astatination, despite the calculated dose amounts of 7,780 Gy and 7,970 Gy to the respective solutions. The "clean" chromatogram of the reaction product containing 200 μg NCS indicated that astatine reactivity was stabilized using even this smaller amount of oxidant.

EXAMPLE 10

Stabilization of Astatine for Electrophilic Astatination at High Radiation Doses Samples of $^{211}$At were prepared and eluted in methanol, and stabilized shortly thereafter with NCS, as described in Example 8. Higher initial $^{211}$At radioactivity levels were used, however, in order to obtain higher radiation doses after 18.7 and 18.3 hours of storage. The samples were then used in the synthesis of SAB under both acidic (one reaction) and neutral (two reactions) conditions, according to the procedures in Example 5. Three HPLC chromatograms of the reaction product solutions after having received a radiation dose of over 40,000 Gy in each case, are shown in FIG. 10.

The use of NCS under both acidic and neutral reaction conditions stabilized $^{211}$At reactivity for electrophilic astatination, despite the calculated dose amounts of 40,922 Gy; 41,181 Gy; and 45,064 Gy; to the respective solutions. As in Example 5, a somewhat higher SAB yield (95%) was obtained under acidic relative to neutral reaction conditions (87% and 88% SAB yield), even though all three reactions provided >85% SAB yield with a "clean" product slate (i.e., few byproducts). The high calculated radiation doses used were representative of those required for commercial astatine reagent solutions having multiple patient doses and/or undergoing several hours of storage (or shipment) time.

Based on Examples 1-10, a strong correlation was found between the relative amounts of the astatine forms At(I) and At(II) and the radiation dose received by the methanol, in which astatine was stored. That is, as the radiation dose increased, the amount of At(II), believed to be a reduced form of astatine, also increased. Storage of astatine under acidic conditions appeared to facilitate the conversion from At(I) to At(II). Further experimentation showed that the astatine form At(II) is significantly less reactive than At(I) for electrophilic astatination.

It has now been demonstrated that astatine can be preserved or stabilized in its At(I) form, which is reactive for electrophilic astatination, by adding a small amount of the oxidant NCS to the methanol, into which freshly made $^{211}$At is eluted, shortly after this elution. The use of even a small amount of this oxidant protected against otherwise detrimental radiolytic effects, even at radiation doses to the methanol exceeding 40,000 Gy Moreover, the stabilized astatine was fully reactive for electrophilic astatination, providing high yields of SAB with good purity.

EXAMPLE 11A

Radio Labeling of Human IgG Using Stabilized Astatine

A vial containing 540 μl of $^{211}$At in methanol, having an initial level of radioactivity of 15.9 mCi (589 MBq) was prepared by the cyclotron irradiation and purification procedures described in Example 1. At 7 minutes after this elution, 100 μg of NCS was added to stabilize the astatine against the formation of At(II). After storage of the $^{211}$At in the NCS-containing methanol for 23 hours, the solution was added to 80 μg of dried BuSTB, in order to synthesize SAB according to the procedures in Example 5. During the storage period, the NCS-containing methanol received a calculated radiation dose 50,046 Gy. As in Example 10, this high calculated radiation dose was representative of those required for commercial astatine reagent solutions. The HPLC chromatogram of the reaction product solution is shown in FIG. 11.

Compared to Example 10, the use of only half the amount (100 μg) of NCS stabilized $^{211}$At reactivity for electrophilic astatination, despite the calculated dose of 50,046 Gy to the solution. As in Example 10, a high yield (85%) of the electrophilic astatination reaction product SAB was obtained with few byproducts.

The SAB-containing reaction product solution was then evaporated and poured into a solution containing 10 mg of human IgG. The reaction yield for the coupling of the α-particle emitter labeled precursor, SAB, with IgG was 70%. At the time of this coupling reaction, the $^{211}$At radioactivity level was 1.7 mCi (63 MBq).

EXAMPLE 11B

Radiolabeling of Human IgG Using Stabilized Astatine

The radiolabeling of human IgG with $^{211}$At was repeated following the same procedures in Example 11 A. The initial quantity of $^{211}$At in methanol, however, was 680 μl, and the contents of the vial had an initial level of radioactivity of 16.7 mCi (618 MBq). During the period that the NCS-containing methanol was stored, it received a calculated radiation dose of 41,768 Gy. Also, 50 μg rather than 80 μg of dried BuSTB were used for the SAB synthesis, and the SAB yield was 80%. The reaction yield for the coupling of the α-particle emitter labeled precursor, SAB, with IgG was 56% (72% if corrected for the 80% SAB yield). At the time of this coupling reaction, the $^{211}$At radioactivity level was 1.86 mCi (69 MBq).

Examples 11A and 11B demonstrate the use of $^{211}$At, having been stored in an oxidant-containing solution for 23 hours, in preparing α-particle emitter labeled IgG. The SAB yields and coupling yields obtained these synthesis were comparable to those obtained for freshly-prepared astatine in methanol.

EXAMPLE 12

Elution of $^{211}$At Into NCS-Containing Methanol/Preparation of Radiolabeled Compounds with High Radioactivity A 200 μl sample of $^{211}$At was prepared as described in Example 1, but eluted directly into an NCS-containing methanol solution, rather than methanol, in order to prevent the conversion of At(I) into At(II) from the outset. The $^{211}$At was then used to prepare radiolabeled human IgG as described in Examples 11A and 11B, except that the $^{211}$At radioactivity level at the time of the coupling reaction was significantly higher, 17.25 mCi (639 MBq), and sufficient for therapeutic applications. The synthesis is outlined below.

| Operation | Time | mCi | Notes |
|---|---|---|---|
| Target Irradiation | 9:32 | 34.87 | This is the activity on the target after 61 min irradiation at 55 μA |
| Distillation | 11:12 | 24.54 | Activity on the 1/16 PEEK tubing, yield 82% (decay corrected) 70% (no decay correction) |
| Elution with NCS/MeOH | 11:20 | 21.62 | 88% elution yield. Elution made with 125 μg NCS/600 μL MeOH, to ensure at least 100 μg NCS in the elution, since normally 10-15% of the volume remains inside the tubing. |
| SAB synthesis | 11:20 | 21.62 | The entire elution was poured over 50 μg STB (no AcOH), 22 min of reaction time, dose received during the reaction time 2,400-2,600 Gy<br>15 μL/0.75 mCi taken for QC, but no HPLC due to failed detector. However, since SAB should be the only non-volatile species, we can estimate the SAB yield from the next step, the evaporation |
| SAB evaporation | 11:42 | 19.87 | The reaction mixture (the entire volume minus the-15 μL/0.75 mCi used for QC) was evaporated. At end of evaporation (12:02) we got 17.25 mCi. 86.8% of the activity remained so we can estimate that the SAB yield was good. It will be confirmed by the next coupling reaction. |
| h-IgG coupling | 12:15 | 17.25 | 10 mg h-IgG/1000 μL was poured (pH 9) over the vial with 17.25 mCi SAB. After 15 min of reaction plus other 5 min of reaction with 0.2 M glycine (termination) the separation with a PD10 column was made. |
| | 12:37 | 16.26 | Loading of PD10 column |
| End procedure | 12:45 | 11.87 | 11.87 mCi (439 MBq) of purified labeled-IgG (II) Coupling yield 73%.<br>After 0.22 μm Millipore filtering it will be ready to inject.<br>considering the 0.75 mCi used for the failed QC we could get even more labeled-IgG |

Total time procedure: 3¼ hours

Stabilization of the $^{211}$At with NCS immediately after its preparation in a cyclotron and recovery by distillation provided the means for synthesizing radiolabeled IgG having an initial radioactivity level of 11.87 mCi (439 MBq) and (after filtration) ready for patient administration in a therapeutically effective amount. Due to the high proportion of the $^{211}$At which, as a result of the stabilization, was incorporated into the radiolabeled IgG, an initial α-particle emitter radioactivity level of only 34.87 mCi (1.29 GBq) was sufficient. This level was easily achieved after only about one hour of target $^{209}$Bi irradiation in the cyclotron. The entire synthesis, from cyclotron bombardment to the preparation of $^{211}$At-labeled IgG, required only about 3¼ hours.

In contrast, without stabilization of the $^{211}$At, previous preparations of radiolabeled IgG having therapeutically effective levels of radioactivity required combining the reaction products from four parallel syntheses, similar to those described above. Furthermore, in order to obtain the same initial level of α-particle emitter labeled IgG as in this experiment, an almost 5-fold increase in the initial α-particle emitter radioactivity level (requiring a comparable increase in the cyclotron target irradiation time) was required. See *High-Level Production of α-Particle-Emitting $^{211}$At and Preparation of $^{211}$At-Labeled Antibodies for Clinical Use*, J NUCL MED. 42:1508-1515 (2001). A comparison of key synthesis parameters, without and with stabilization (previous vs. current), is shown below.

| | Irradiation time, 55 μA | GBq on target | GBq distilled | % recovered after distillation | MBq of SAB | SAB % yield | MBq of mAb | Coupling % |
|---|---|---|---|---|---|---|---|---|
| previous | 4.5 hours | 6.44 | 3.74 | 73 | 0.784 | 21 | 0.444 | 80 |
| Current | 1 | 1.29 | 0.908 tubing 0.8 in elution | 82 | 0.67 | 84 | 0.439 (hIgG) | 73 |

The elution of the distillation trap made with NCS/MeOH not only provided the "safety-net" of the presence of the NCS since the very beginning, but it also seemed to be more efficient, in $^{211}At$ recovery from the distillation device, than the elution made with methanol alone. With methanol alone, the best elution recovery achieved in prior experiments was 75%, but in a distillation run with much lower activity on the target. Furthermore, in the past it was observed that higher the activity on the target resulted in lower the efficiency of the elution.

EXAMPLE 13

Astatine Stabilization for Preparing Therapeutically Effective Compositions

A sample of $^{211}At$ was prepared by cyclotron bombardment of $^{209}Bi$, volatilized from this target, and eluted in methanol. The sample was divided into two separate vials containing $^{211}At$ in methanol, the contents of which were used in the synthesis of SAB according to the procedures described in Example 5. The contents of the first vial were used almost immediately in the electrophilic astatination reaction. The contents of the second vial were added to 100 μg of NCS, allowed to stand for a storage period of 104 minutes, and then used for the SAB synthesis. No additional NCS was used in the synthesis. The reaction product solution associated with the first vial received a calculated radiation dose rate of 3.94 Gy/s and a calculated total dose of 6,152 Gy over the course of the radiolabeling reaction. The reaction product solution associated with the second vial received a calculated radiation dose rate of 2.27 Gy/s and a calculated total dose of 17,026 Gy over the course of the storage period and subsequent radiolabeling reaction.

This experiment was designed to simulate expected levels of initial α-emitter solution radioactivity (about 22-23 mCi), as well as radiation dose rate (3-6 Gy/s) and total radiation dose (about 6,000-8,000 Gy) received by the reaction product solution, in this case utilizing a reaction solution volume of 300 μL and a reaction time of 30 min. The HPLC chromatograms of the reaction product solutions obtained using the contents of the first and second vials are shown in FIGS. 12 and 13, respectively.

The results again conclusively demonstrate the benefit of adding an oxidant, in this case NCS, to the $^{211}At$ solution prior to its use for electrophilic astatination. The reaction yield of the radiolabeled precursor SAB using $^{211}At$ from the first vial (in the absence of an oxidant) was only 15%, compared to 67% obtained using the $^{211}At$ from the second vial. This significant yield improvement was despite the fact that the contents of the second vial were subjected to a storage period, resulting in a much higher radiation dose received. Moreover, the oxidant NCS in this experiment was not added until 21 minutes after the elution of freshly prepared $^{211}At$ in methanol, during which time the methanol had already received a calculated dose rate and total radiation dose of 3.66 Gy/s and 4613 Gy, respectively. Based on these results, stabilization of the α-particle emitter is beneficial not only during storage but also during the course of radiolabeling reactions, and in particular when the reaction solution receives a high radiation dose, representative of therapeutic applications. Stabilization of the α-particle emitter is thus a significant consideration, even with freshly-prepared solutions containing the α-particle emitter, such as $^{211}At$/methanol solutions.

EXAMPLE 14

Astatine Stabilization at Very High Radiation Doses

An additional two samples of $^{211}At$ in methanol were prepared as described in Example 1, with a significantly higher level of radioactivity than even the sample described in Example 11A (used in the preparation of radiolabeled human IgG). To these samples, 100 μg of NCS was added to stabilize the astatine against the formation of At(II). The $^{211}At$ samples in NCS-containing methanol were stored for some time before being used to synthesize SAB according to the procedures in Example 5. No additional NCS was used in the synthesis. During the storage and subsequent reaction periods, the solutions received calculated radiation doses of 71,500 Gy and 125,086 Gy, respectively. The HPLC chromatogram of the reaction product solution receiving the higher dose is shown in FIG. 14. The $^{211}At$ sample in NCS-containing methanol was stored for 18 hours in this case.

The SAB yields obtained for the reaction solutions receiving 71,500 Gy and 125,086 Gy were 65% and 82%, respectively, with a very clean HPLC profile in both cases. These results further demonstrate the ability of an oxidant to allow practical preparations of $^{211}At$ labeled compounds at therapeutically effective radioactivity levels, even when the reaction solution receives very high radiation doses. The radiation doses received in these cases are representative of the dose received in 5 hours by 500 μL of solution, when the initial radioactivity level of the α-particle emitter is 49 mCi and 86 mCi, respectively.

EXAMPLE 15

Astatine Stabilization with Various Oxidants

Additional samples of $^{211}At$ in methanol were prepared as described in Example 1 and then used in the synthesis of SAB according to the procedures described in Example 5. Rather than NCS, various other oxidants were added to the $^{211}At$/methanol solution samples. Oxidant addition was performed as quickly as possible following the elution of $^{211}At$ in methanol. The oxidant-stabilized solutions were then allowed to stand for specific storage periods, over which time the radiation dose and dose rate to each solution could be determined. At a chosen time, the solution for each experiment was poured into a vial containing BuSTB and acetic acid. The solution amount was adjusted to maintain the same $^{211}At$ concentration in each case. Times, volumes, and radioactivity levels were recorded for accurate calculation of radiation dose rates and total doses.

Table 1 below provides a listing of each oxidant used for $^{211}At$ stabilization, the amount used (in micromoles), the concentration (in % by weight), the total radiation dose received (Gy), the dose rate received (Gy/s), and the % yield of SAB.

TABLE 1

| Compound | μmol/wt-% | Gy | Gy/s | % SAB |
|---|---|---|---|---|
| Sodium hypochlorite (NaClO) | 0.5/0.037 | 51301 | 0.58 | 39 |
| NaClO | 1.2/0.099 | 61325 | 2.39 | 91.4 |
| Sodium chlorite ($NaClO_2$) | 1.5/0.170 | 47248 | 0.53 | 86 |
| $NaClO_2$ | 5/0.514 | 48553 | 1.17 | 75 |
| $NaClO_2$ | 5/0.452 | 50016 | 0.52 | 77 |
| $NaClO_2$ | 5/0.452 | 51402 | 0.57 | 82 |
| $NaClO_2$ | 1.5/0.128 | 57377 | 0.73 | 80 |
| $NaClO_2$ | 5/0.696 | 65594 | 3.53 | 85 |

TABLE 1-continued

| Compound | μmol/wt-% | Gy | Gy/s | % SAB |
|---|---|---|---|---|
| Sodium chlorate ($NaClO_3$) | 5/0.532 | 50894 | 0.54 | 49 |
| Chloramine-T | 1.5/0.321 | 51380 | 0.57 | 13 |
| Chloramine-T | 5/1.746 | 72755 | 3.3 | 76 |
| 2-Chloro-4-fluorobenzenesulfonyl chloride | 5/1.636 | 64661 | 2.7 | 66 |
| 2-Chloro-1,3,2-benzodioxaphosphorin-4-one | 5/2.53 | 67980 | 2.34 | 65 |
| Ammonium cerium (IV) nitrate $[(NH_4)Ce(NO_3)_6]$ | 5/3.187 | 32380 | 0.36 | 60 |
| $(NH_4)Ce(NO_3)_6$ | 5/3.916 | 71997 | 2.6 | 86 |

The HPLC chromatograms of the reaction product solutions corresponding to the experiments described in rows 4 and 14 of Table 1 above, are shown in FIGS. 15 and 16, respectively. In these experiments, the yields of SAB obtained by stabilization of $^{211}$At with 5 μmol of the oxidants sodium chlorite and ammonium cerium (IV) nitrate, were 75% and 60%, respectively. Again, the protective fimction of the oxidant is demonstrated in the case of radiolabeling reaction solutions having been exposed to radiation levels representative of those expected in actual practice.

The results of this study show that a wide variety of oxidants are suitable for the stabilization of α-particle emitters such as $^{211}$At, allowing for the radiolabeling of compounds in high yields. Up to a point, and maintaining other variables constant, increasing the amount of oxidant generally resulted in increased SAB yields. In view of those results, coupled with the present disclosure, one could routinely utilize the above experimental procedures to evaluate other oxidants and optimize the amount of added oxidant.

Consequences of the Experimental Results

The findings and associated methodologies described here, which relate to the stabilization of astatine at high radiation doses to the solution, are independent of the molecule to be astatinated. Any molecule to be labeled with $At^+$ can benefit from the present invention. The radiolabeling procedure which follows as a result of the discoveries described here is very simple. It is fast, results in low radiation doses received by the operator (i.e., it is safe), and is easily automated.

Based on experiments performed to date and given the doses that can now be stored in astatine-containing solutions, with the astatine being made at Duke University's cyclotron, astatine can be sent to remote locations, and even overseas. This advance is particularly important because there are only a few cyclotrons (less than 5 in the United States) capable of producing therapeutic levels of $^{211}$At. In the experiment where astatine was stored in a solution receiving up to 50,046 Gy, this would be equivalent to sending 35 mCi radioactivity in 500 μL for 5 hours, where 22 mCi would arrive on site. New York City could be reached from Duke University in this time. This 22 mCi of activity that a lab located at 5 hours from the Duke cyclotron could receive is almost the same as that used to start the chemical labeling procedure in the protein labeling experiment performed above. This radioactivity level would be sufficient for administration to patients.

The procedure is so simple that it is only necessary to send 2 vials, for example in a kit: one vial with the $^{211}$At/methanol/NCS and the other vial with 50 μg of dried STB. Upon arrival of the kit, the users only need to pour the vial containing the radioactive material over the STB vial, wait 15 min (for the SAB formation reaction), evaporate the solution, and then pour a solution of the desired antibody over the dried SAB to couple the antibody to the SAB. After purification in a PDIO column, the radiolabeled antibody would be ready. The limit of the radioactivity and doses that can be stored are significantly higher than in the past, based on the findings that essentially all of the $^{211}$At was reactive, even when the dose to the solution containing it was over 50,000 Gy. Alternatively, if radiation doses beyond the protection capacity of the oxidant in a single vial would be required (no limit has been found to date experimentally; however, it is possible that this might occur where a very high level of $^{211}$At activity would be required, e.g. to meet the activity needed for overseas shipment), more than one $^{211}$At/methanol/NCS vial could be sent or provided in the kit.

About Astatine Chemistry

The use of $At^+$ for electrophilic astatination reactions allows the labeling of many kinds of molecules, is reliable, and can produce stable molecules. Furthermore, using an oxidant to stabilize the $At^+$, it is now possible to reach the high levels of activities and radiation doses necessary for clinical use. It is also possible to store very high doses and send the stabilized astatine to a laboratory located at least several hours away from the cyclotron. Because of the reaction efficiencies resulting from the stabilization approach, sufficient astatine for patient use can be generated with just one hour of cyclotron irradiation time. Based on the discovery of astatine stabilization, this element and other alpha-particle emitters are now ready for therapeutic use extensively in wide-ranging applications.

Importantly, the stabilization described above is completely independent of the molecule to be astatinated. It could be used for labeling STB or any other molecule capable of undergoing electrophilic substitution. The application of the invention to the radiolabeling of peptides and antibodies is most apparent. However, the application of many new molecules to alpha-particle emitter radiolabeling will be recognized in the years to come. The present invention will therefore apply equally well to the labeling of these molecules. In fact, the invention will benefit any practical application where radiolabeling with alpha-particle emitters having high radioactivity levels is required.

Methanol has the advantage that it can dissolve molecules of widely ranging hydophilicity/hydrophobicity, from somewhat lipophilic molecules (like STB) to very hydrophilic molecules. Methanol may also act in concert with the NCS to stabilize astatine. Therefore, it is envisioned that the $^{211}$At/NCS/methanol system, in particular, will be usefull for many, if not most, new molecules exhibiting promise in the field of radiolabeling. However, other alcohols, and mixtures of alcohols, can also be employed, depending on the specific application. For example, butanol may be used to dissolve more lipophilic molecules. Secondary and tertiary alcohols may have properties desirable for other types of molecules. As such, the type of solution can be adapted to the type of molecule to be radiolabeled.

The discoveries described here and relating to astatine solution chemistry apply generally to alpha-particle emitters other than astatine, and include those having a short half-life.

What is claimed is:

1. A method for preparing a $^{211}$ At labeled pharmaceutical, the method comprising the steps of:

(a) stabilizing $^{211}$ At in a solution containing an oxidant, wherein said solution forms reducing species as a result of radiolytic effects of said $^{211}$ At and wherein said oxidant is present in an effective amount for stabilizing said $^{211}$ At against said radiolytic effects; and thereafter (b) reacting said $^{211}$At with a pharmaceutical having a reactive astatination site to provide the $^{211}$At labeled pharmaceutical, wherein said solution containing an oxidant receives a total radiation dose of at least about 1,330 Gy prior to said reacting step, and wherein the $^{211}$At labeled pharmaceutical has an initial radioactivity level of at least about 35% of an initial $^{211}$At radioactivity added in said reacting step (b).

2. The method of claim 1, further comprising, prior to said stabilizing step, preparing said $^{211}$At by irradiation of an accelerator target.

3. The method of claim 2, further comprising, after preparing said $^{211}$At and prior to said stabilizing step, purifying said $^{211}$At by distillation.

4. The method of claim 3, wherein said stabilizing step comprises eluting said $^{211}$At in said solution containing an oxidant.

5. The method of claim 1, wherein said reacting step is carried out at least 30 minutes after said stabilizing step.

6. The method of claim 1, wherein said radiation dose is at least about 2,000 Gy.

7. The method of claim 1, wherein said radiation dose is from about 3,000 to about 150,000 Gy.

8. The method of claim 1, wherein said pharmaceutical is a peptide, a polypeptide, a protein, an antibody, or an antibody fragment.

9. A method for preparing a $^{211}$At labeled compound, the method comprising the steps of:

stabilizing $^{211}$At in a solution containing an oxidant, wherein said solution forms reducing species as a result of radiolytic effects of said $^{211}$At; and thereafter reacting said $^{211}$At with a compound having a reactive astatination site to provide the $^{211}$At labeled compound, wherein said $^{211}$At in said solution has an initial radioactivity level of at least about 15 mCi (555 MBq), wherein said oxidant is selected from the group consisting of a halogenated organic compound, a peroxide, an organic acid, and a salt of an anion selected from the group consisting of permanganate, chromate, dichromate, perborate, perphosphate, persulfate, perchlorate, chlorate, chlorite, hypochlorite, perbromate, bromate, bromite, hypobromite, periodate, iodate, iodite, hypoiodite, and bismuthate, and wherein said oxidant is present in an effective amount for stabilizing said $^{211}$At against said radiolytic effects.

10. The method of claim 9, wherein said $^{211}$At labeled compound has an initial radioactivity level that is at least about 20% of said initial radioactivity level of said $^{211}$At in said solution.

11. The method of claim 9, further comprising, prior to said stabilizing step, preparing said $^{211}$At by irradiation of an accelerator target.

12. The method of claim 11, further comprising, after preparing said $^{211}$At and prior to said stabilizing step, purifying said $^{211}$At by distillation.

13. The method of claim 12, wherein said stabilizing step comprises eluting said $^{211}$At into said solution containing an oxidant.

14. The method of claim 9, wherein said reacting step is carried out at least 30 minutes after said stabilizing step.

15. The method of claim 9, wherein said $^{211}$At labeled compound is provided in a radiochemical reaction yield of at least about 30%.

16. The method of claim 9, wherein said reactive astatination site is selected from the group consisting of an electrophilic astatine substitution site, a nucleophilic astatine substitution site, an astatine complexation site, an astatine exchange site, and an astatine-metal bonding site.

17. The method of claim 16, wherein said reactive astatination site is an electrophilic astatine substitution site, and wherein said compound having said electrophilic astatine substitution site is a peptide, a polypeptide, a protein, an antibody, or an antibody fragment that is modified to have said electrophilic astatine substitution site.

18. The method of claim 16, wherein said compound having said electrophilic astatine substitution site is an organometallic precursor.

19. The method of claim 1, wherein said stabilizing step comprises preparing said solution containing said $^{211}$At, wherein said oxidant is present in said solution prior to adding $^{211}$At or added separately.

20. The method of claim 9, wherein said stabilizing step comprises preparing said solution containing said $^{211}$At, wherein said oxidant is present in said solution prior to adding $^{211}$At or added separately.

21. A method for preparing a $^{211}$At labeled compound, the method comprising the steps of:

stabilizing $^{211}$At in a solution containing an oxidant, wherein said solution forms reducing species as a result of radiolytic effects of said $^{211}$At; and thereafter reacting said $^{211}$At with a compound having a reactive astatination site to provide the $^{211}$At labeled compound, wherein said solution containing an oxidant receives a total radiation dose of at least about 1,330 Gy prior to said reacting step, wherein said oxidant is selected from the group consisting of a halogenated organic compound, a peroxide, an organic acid, and a salt of an anion selected from the group consisting of permanganate, chromate, dichromate, perborate, perphosphate, persulfate, perchlorate, chlorate, chlorite, hypochlorite, perbromate, bromate, bromite, hypobromite, periodate, iodate, iodite, hypoiodite, and bismuthate, and wherein said oxidant is present in an effective amount for stabilizing said $^{211}$At against said radiolytic effects.

22. The method of claim 20, wherein the oxidant is a halogenated organic compound or a peroxide.

23. The method of claim 21, wherein the oxidant is a halogenated organic compound.

24. The method of claim 22, wherein the halogenated organic compound is a halo succinimide.

25. The method of claim 23, wherein the halosuccinimide is N-chlorosuccinimide.

* * * * *